United States Patent
Xu et al.

(10) Patent No.: US 10,080,771 B2
(45) Date of Patent: Sep. 25, 2018

(54) COMPOSITIONS AND METHODS FOR GENERATION OF HUMAN EPITHELIAL STEM CELLS

(71) Applicant: The Trustees of the University of Pennsylvania, Philadelphia, PA (US)

(72) Inventors: Xiaowei Xu, Monmouth Junction, NJ (US); Ruifeng Yang, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 82 days.

(21) Appl. No.: 15/009,157

(22) Filed: Jan. 28, 2016

(65) Prior Publication Data

US 2016/0213717 A1   Jul. 28, 2016

Related U.S. Application Data

(60) Provisional application No. 62/108,879, filed on Jan. 28, 2015.

(51) Int. Cl.
*A61K 35/35* (2015.01)
*A61K 35/36* (2015.01)
*C12N 5/071* (2010.01)

(52) U.S. Cl.
CPC ............ *A61K 35/36* (2013.01); *C12N 5/0627* (2013.01); *C12N 5/0628* (2013.01); *C12N 2501/11* (2013.01); *C12N 2501/115* (2013.01); *C12N 2501/155* (2013.01); *C12N 2501/385* (2013.01); *C12N 2506/45* (2013.01)

(58) Field of Classification Search
CPC ..................................................... A61K 35/36
See application file for complete search history.

(56) References Cited

U.S. PATENT DOCUMENTS

2011/0021599 A1\* 1/2011 Cotsarelis .......... A01K 67/0275
                                              514/44 A
2013/0059386 A1\* 3/2013 Yamanaka ......... C07K 14/4702
                                              435/455

OTHER PUBLICATIONS

Williams et al. (2012, Cell, vol. 149, 1 page slide).\*
Veraitch et al. (2013, J. Investigative Dermatology, vol. 133, pp. 1479-1488).\*
Roche Product Information for EGF (published Jun. 2011, Version 05, Cat. No. 11 376 454 001, 1 page).\*
Benjamini, Yoav et al., "Controlling the False Discovery Rate: A Practical and Powerful Approach to Multiple Testing", Journal of the Royal Statistical Society, Series B (Methodological), 57(1): 289-300 (1995).
Bilousova, Ganna et al., "Differentiation of Mouse Induced Pluripotent Stem Cells into a Multipotent Keratinocyte Lineage", Journal of Investigative Dermatology, 131: 857-864 (2011).
Cotsarelis, George et al., "Towards a molecular understanding of hair loss and its treatment", Trends in Molecular Medicine, 7(7): 293-301 (2001).
Costarelis, George et al., "Label-Retaining Cells Reside in the Bulge Area of Pilosebaceous Unit: Implications for Follicular Stem Cells, Hair Cycle, and Skin Carcinogenesis", Cell, 61: 1329-1377 (1990).
Dimos, John T. et al., "Induced Pluripotent Stem Cells Generated from Patients with ALS Can Be Differentiated into Motor Neurons", Science, 321: 1218: 1221 (2008).
Du, Pan et al., "Lumi: a pipeline for processing Illumina microarray", Bioinformatics, 24(13): 1547-1548 (2008).
Dubois, Nicole C. et al., "SIRPA is a specific cell-surface marker for isolating cardiomyocytes derived from human pluripotent stem cells", Nature Biotechnology, 29(11): 1011-1018 (2011).
Ebert, Allison D. et al., "Induced pluripotent stem cells from a spinal muscular atrophy patient", Nature, 457: 277-281 (2009).
Ehama, Ritsuko et al., "Hair Follicle Regeneration Using Grafted Rodent and Human Cells", Journal of Investigative Dermatology, 127: 2106-2115 (2007).
Garza, Luis A. et al., "Blad scalp in men with androgenetic alopecia retains hair follicle stem cells but lacks CD200-rich and CD34-positive hair follicle progenitor cells", The Journal of Clinical Investigation, 121(2): 613-622 (2011).
Ghosh, Zhumur et al., "Dissecting the Oncogenic and Tumorigenic Potential of Differentiated Human Induced Pluripotent Stem Cells and Human Embryonic Stem Cells", Cancer Res., 71(14): 5030-5039 (2011).
Guenou, Hind et al., "Human embryonic stem-cell derivatives for full reconstruction of the pluristratified epidermis: a preclinical study", Lancet, 374: 1745-53 (2009).
Hanna, Jacob et al., "Treatment of Sickle Cell Anemia Mouse Model with iPS Cells Generated from Autologous Skin", Science, 318: 1920-1923 (2007).
Ito, Mayumi et al., "Wnt-dependent de novo hair follicle regeneration in adult mouse skin after wounding", Nature, 447: 316-320 (2007).
Ito, Mayumi et al., "Stem cells in the hair follicle bulge contribute to wound repair but not to homeostasis of the epidermis", Nature Medicine, 11(12): 1351-1354 (2005).
Itoh, Munenari et al., "Generation of keratinocytes from normal and recessive dystrophic epidermolysis bullosa-induced pluripotent stem cells", PNAS, 108(21): 8797-8802 (2011).
Jaks, Viljar et al., "Lgr5 marks cycling, yet long-lived, hair follicle stem cells", Nature Genetics, 40(11): 1291-1299 (2008).
Janich, Peggy et al., "The circadian molecular clock creates epidermal stem cell heterogeneity", Nature, 480: 209-214 (2011).
Kishimoto, Jiro et al., "Selective activation of the versican promoter by epithelial-mesenchymal interactions during hair follicle development", Proc. Natl. Acad. Sci. USA, 96: 7336-7341 (1999).
Lee, Gabsang et al., "Modelling pathogenesis and treatment of familial dysautonomia using patient-specific iPSCs", Nature, 461: 402-406 (2009).

(Continued)

*Primary Examiner* — Thaian N Ton
*Assistant Examiner* — David A. Montanari
(74) *Attorney, Agent, or Firm* — Kathleen D. Rigaut; Dann, Dorfman, Herrell and Skillman, P.C.

(57) ABSTRACT

Compositions and methods for generating human epithelial stem cells from induced pluripotent stem cells are disclosed. Also disclosed are methods of using cells so generated in hair transplant procedures.

3 Claims, 23 Drawing Sheets
(18 of 23 Drawing Sheet(s) Filed in Color)

(56) References Cited

OTHER PUBLICATIONS

Liu, Yaping et al., "Keratin 15 Promoter Targets Putative Epithelial Stem Cells in the Hair Follicle Bulge", 963-968 (2003).

Metallo, Christian M. et al., "Retinoic Acid and Bone Morphogenetic Protein Signaling Synergize to Efficiently Direct Epithelial Differentiation of Human Embryonic Stem Cells", Stem Cells, 26: 372-380 (2008).

Morris, Rebecca J. et al., "Capturing and profiling adult hair follicle stem cells", Nature Biotechnology, 22(4): 411-417 (2004).

Nakagawa, Masato et al., "Generation of induced pluripotent stem cells without Myc from mouse and human fibroblasts", Nature Biotechnology, 26(1): 101-106 (2008).

Nissan, Xavier et al., "Functional melanocytes derived from human pluripotent stem cells engraft into pluristratified epidermis", PNAS, 108(36): 14861-14866 (2011).

Ohyama, Manabu et al., "Characterization and isolation of stem cell-enriched human hair follicle bulge cells", The Journal of Clinical Investigation, 116(1): 249-260 (2006).

Park, In-Hyun et al., "Reprogramming of human somatic cells to pluripotency with defined factors", Nature, 451: 141-146 (2007).

Raya, Angel et al., "Disease-corrected haematopoietic progenitors from Fanconi anaemia induced pluripotent stem cells", Nature, 460: 53-59 (2009).

Roh, Cecelia et al., "Multi-potentiality of a new immortalized epithelial stem cell line derived from human hair follicles", In Vitro Cell Dev. Biol.—Animal, 44: 236-244 (2008).

Sanchez, Alex, "Linear Models and Empirical Bayes Methods for Microarray Data Analysis", University of Barcelona, Apr. 13, 2009.

Snippert, Hugo J. et al., "Lgr6 Marks Stem Cells in the Hair Follicle that Generate all Cell Lineages of the Skin", Science, 327: 1385-1389 (2010).

Soldner, Frank et al., "Parkinson's Disease Patient-Derived Induced Pluripotent Stem Cells Free of Viral Reprogramming Factors", Cell, 136: 964-977 (2009).

Takahashi, Kazutoshi et al., "Induction of Pluripotent Stem Cells from Mouse Embryonic and Adult Fibroblast Cultures by Defined Factors", Cell, 126: 663-676 (2006).

Tang, Chad et al., "An antibody against SSEA-5 glycan on human pluripotent stem cells enables removal of teratoma-forming cells", Nature Biotechnology, 29(9): 829-834 (2011).

Tong, Man et al., "Mice generated from tetraploid complementation competent iPS cells show similar developmental features as those fro mES cells but are prone to tumorigenesis", Cell Research, 21: 1634-1637 (2011).

Trempus, Carol S. et al., "Enrichment for Living Murine Keratinocytes from the Hair Follicle Bulge with the Cell Surface Marker CD34", J. Invest. Dermatol., 120: 501-511 (2003).

Veraitch, Ophelia et al., "Human Induced Pluripotent Stem Cell-Derived Ectodermal Precursor Cells Contribute to Hair Follicle Morphogenesis In Vivo", J. Invest. Dermatol., 133: 1479-1488 (2013).

Yang, Ruifeng et al., "Generation of Melanocytes from Induced Pluripotent Stem Cells", J. Invest. Dermatol., 131: 2458-2466 (2011).

Zheng, Ying et al., "Organogenesis from Dissociated Cells: Generation of Mature Cycling Hair Follicles from Skin-Derived Cells", J. Invest. Dermatol., 124: 867-876 (2005).

Zheng, Ying et al., "Mature Hair Follicles Generated from Dissociated Cells: A Universal Mechanism of Folliculoneogenesis", Developmental Dynamics, 239: 2619-2626 (2010).

\* cited by examiner

Fig. 1A
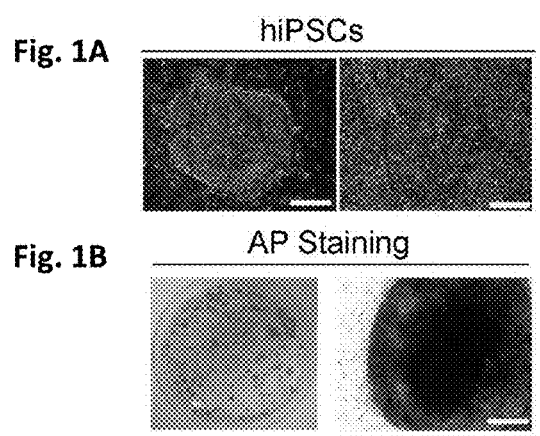
Fig. 1B
Fig. 1C
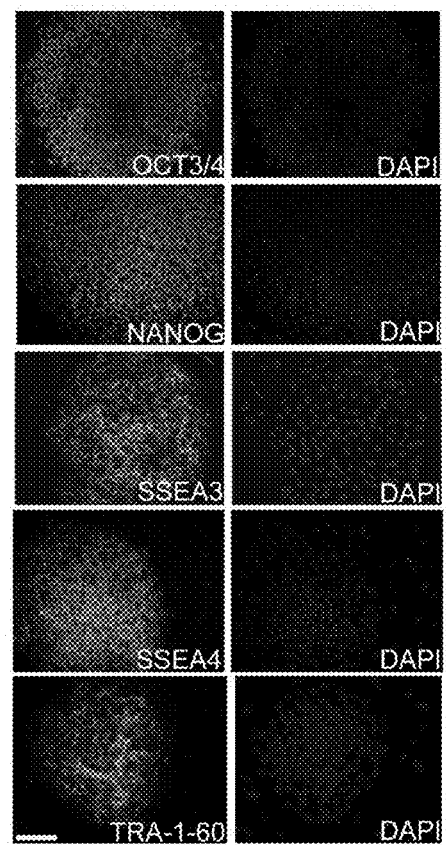

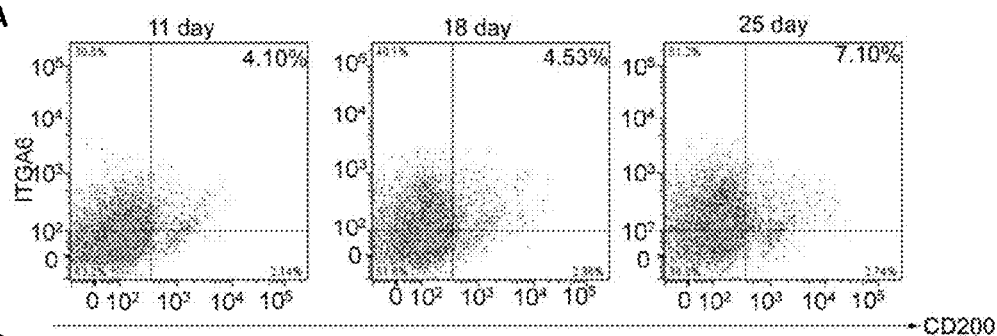
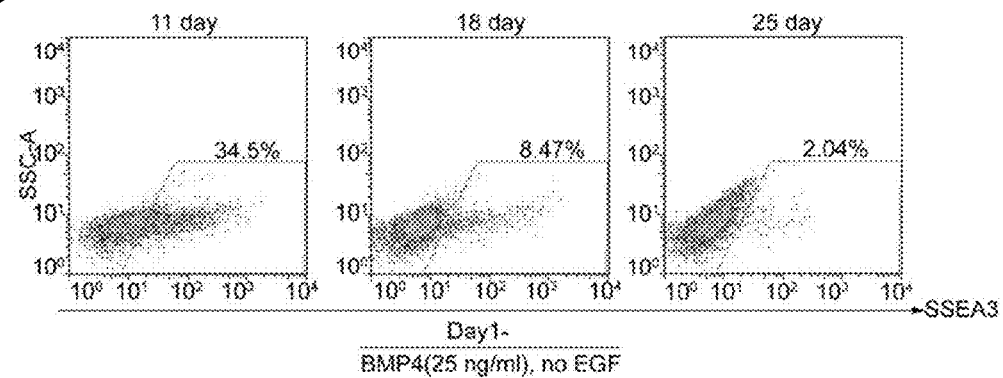
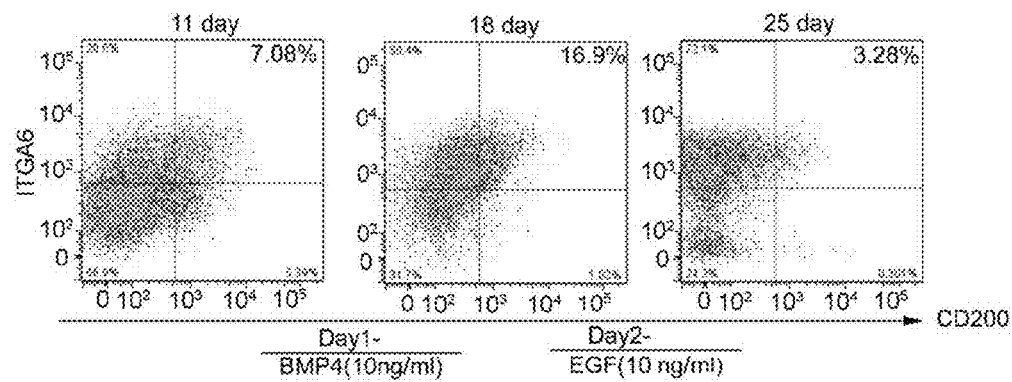
Fig. 8

Fig. 10A
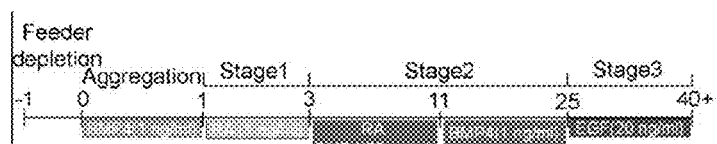
Fig. 10B
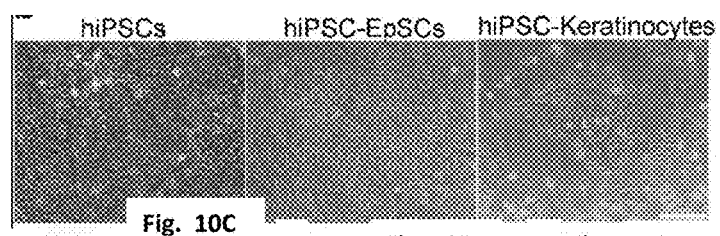
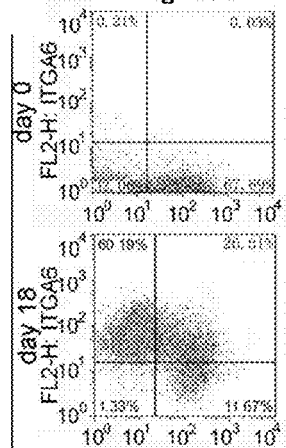 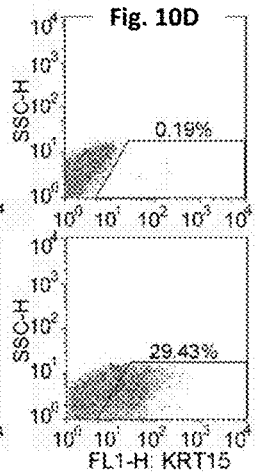 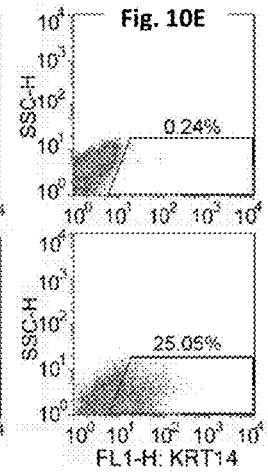
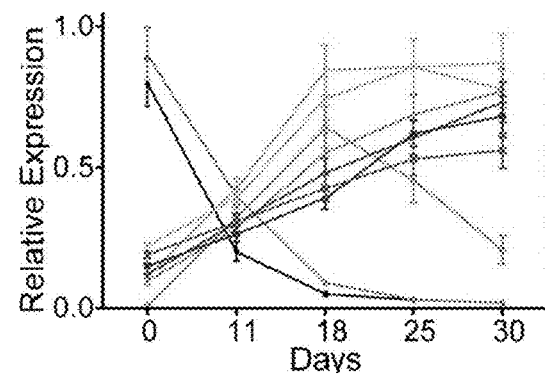
Fig. 10F
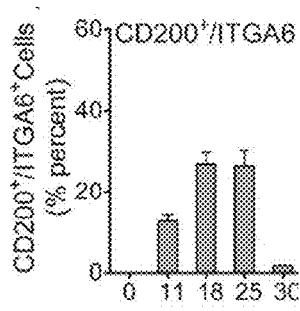
Fig. 10G
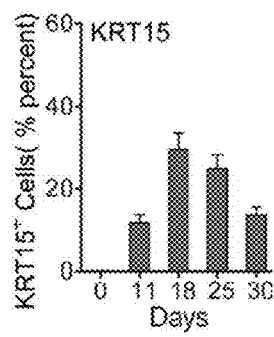
Fig. 10H
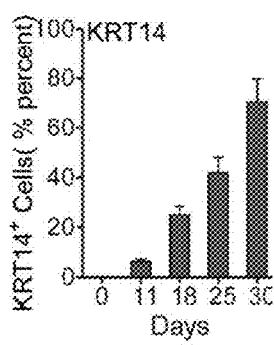
Fig. 10I

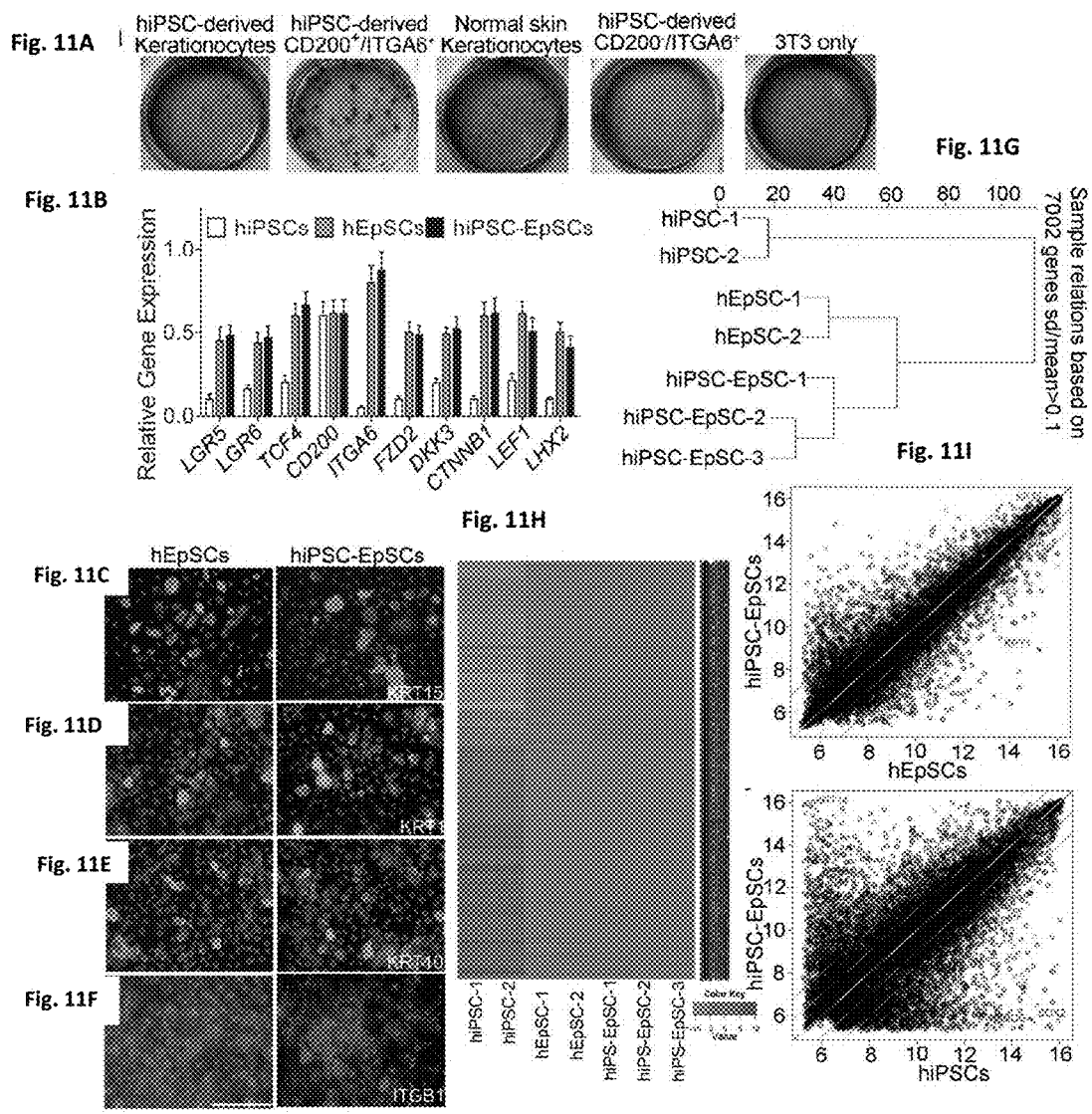

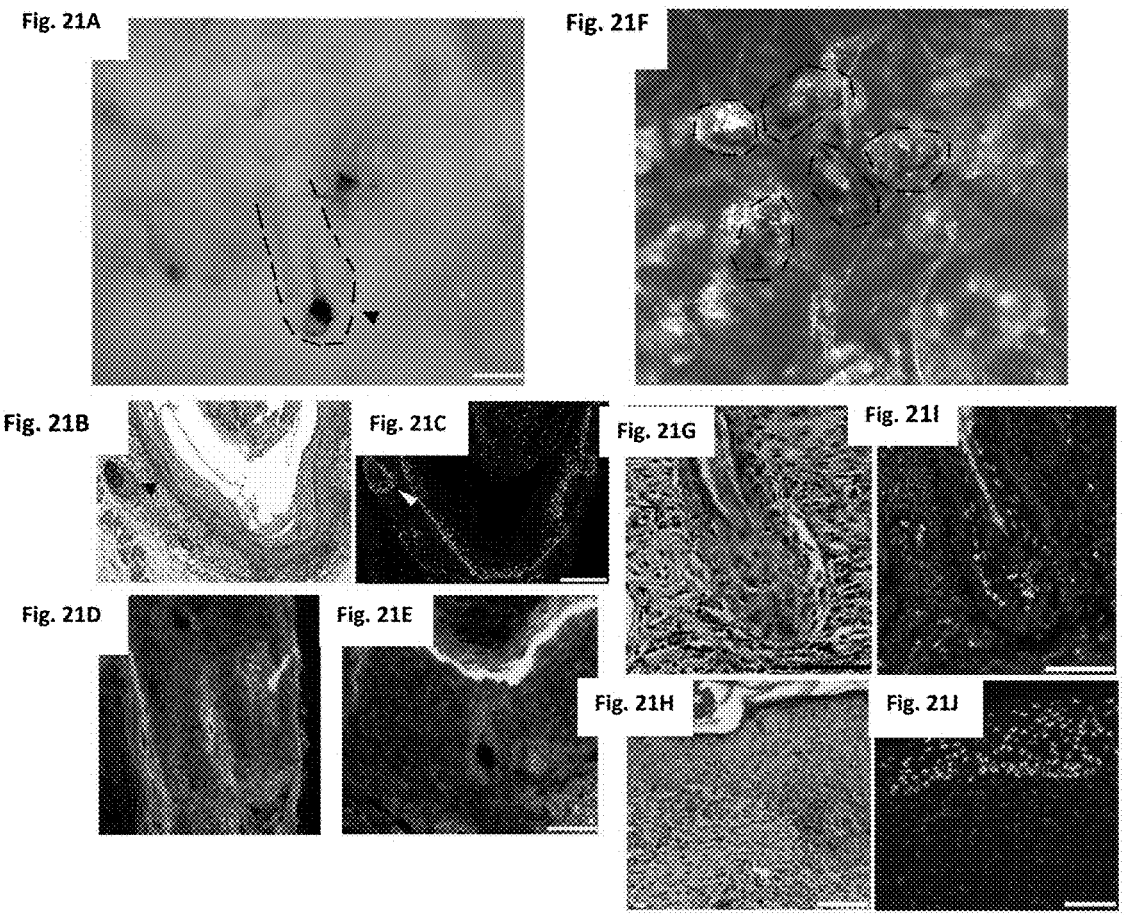

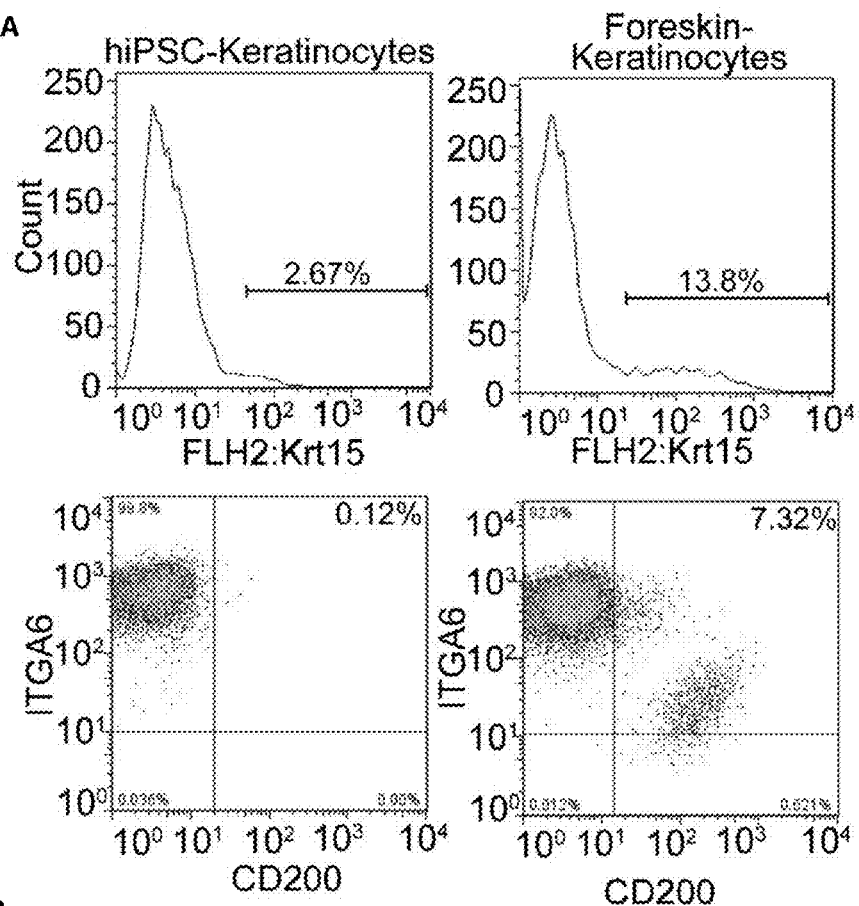
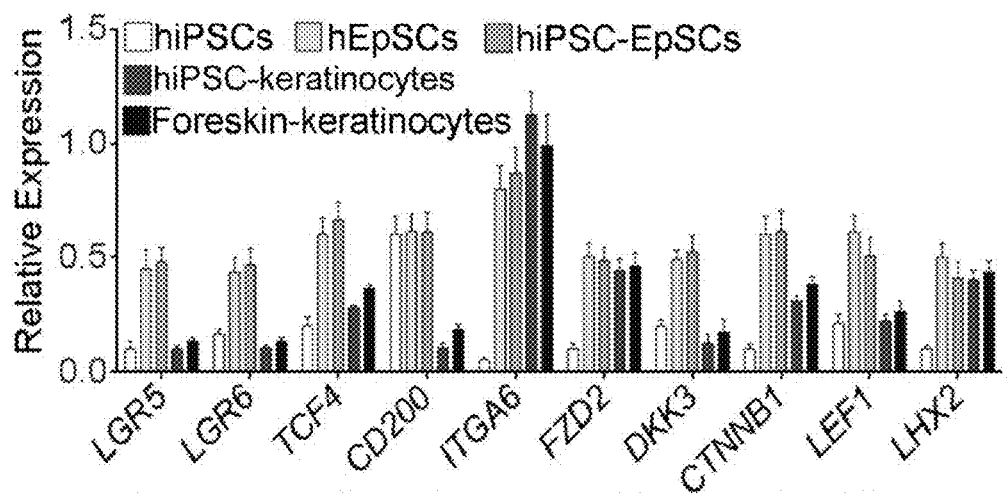
Fig. 22A
Fig. 22B

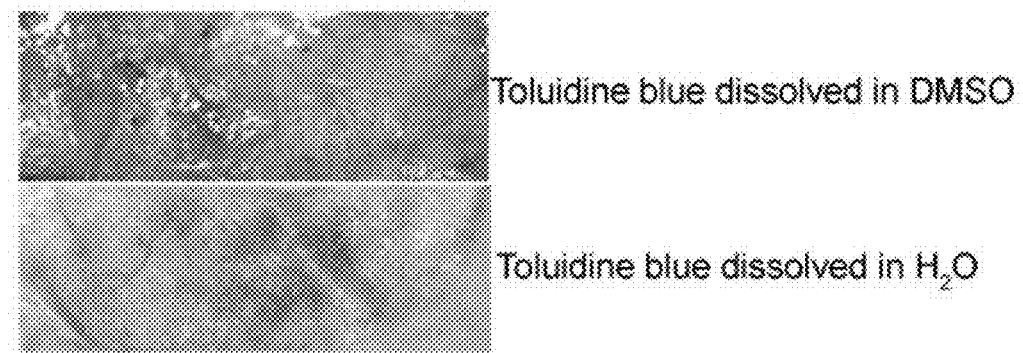
Fig. 23
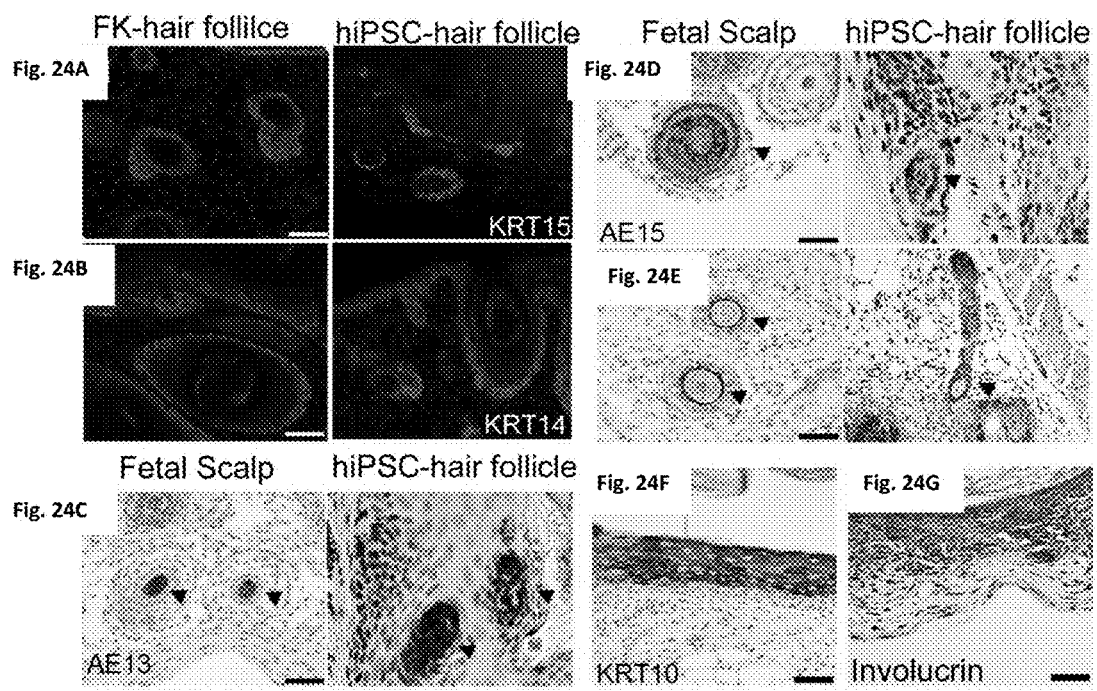

Fig. 25A
Fig. 25B
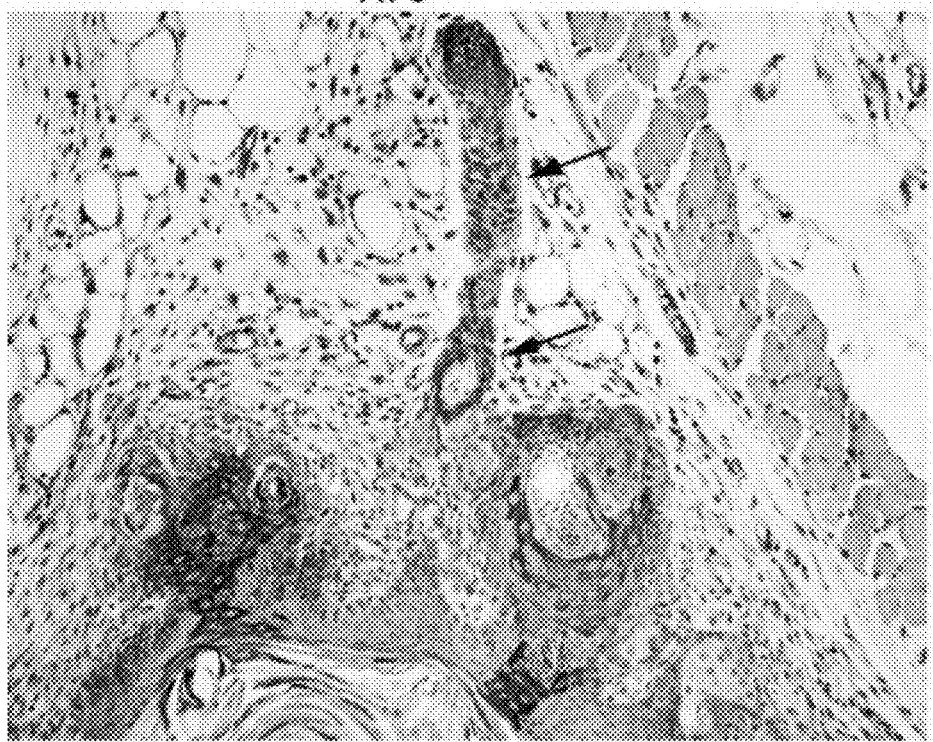
Fig. 26

Fig. 27A
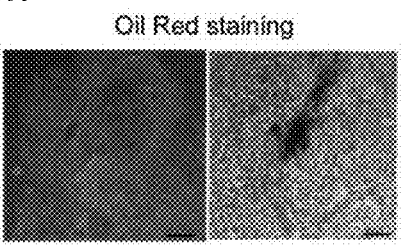
Oil Red staining
Fig. 27B
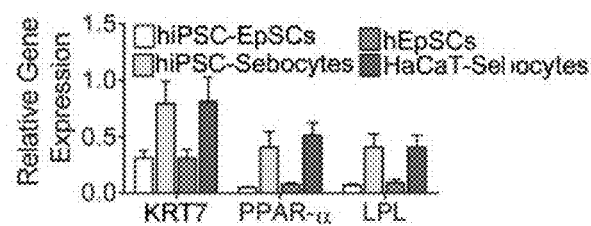
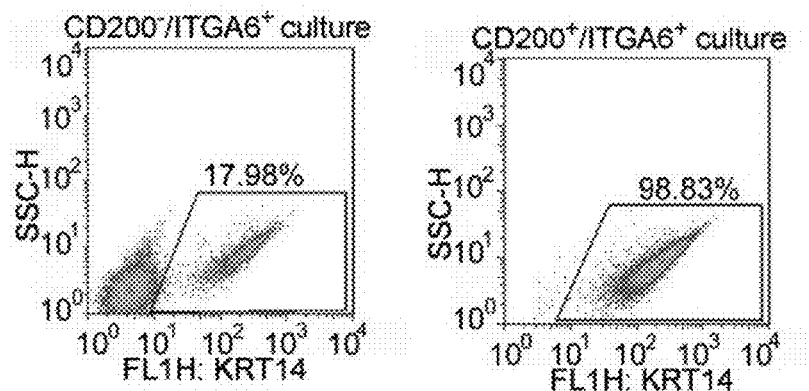
Fig. 28

COMPOSITIONS AND METHODS FOR GENERATION OF HUMAN EPITHELIAL STEM CELLS

CROSS-REFERENCE TO RELATED APPLICATIONS

The present application claims the benefit of U.S. Provisional Patent Application No. 62/108,879, filed Jan. 28, 2015, the entire disclosure of which is incorporated by reference herein.

FIELD OF THE INVENTION

This invention relates to fields of stem cell isolation and propagation and regeneration of desired tissue types. More specifically, the invention provides methods for generating epithelial stem cells from induced pluripotent stem cells (iPSC) and methods of use thereof in regenerative medicine.

BACKGROUND OF THE INVENTION

Several publications and patent documents are cited throughout the specification in order to describe the state of the art to which this invention pertains. Each of these references are incorporated herein as though set forth in full.

Directed differentiation of pluripotent stem cells into a variety of cell types opens new possibilities for regenerative medicine (1-6). Epithelial stem cells (EpSCs) in the hair follicle bulge are required for hair follicle growth and cycling, while also contributing to wound healing (7-10). Human EpSCs (hEpSCs) in the hair follicle express CD200, ITGA6 and cytokeratin-15 (KRT15)(11, 12) but their isolation and propagation for tissue engineering purposes remains a challenge. Generating sufficient numbers of hEpSCs is crucial for treatment of hair loss and other degenerative skin diseases (9, 13).

It has been shown that human embryonic stem cells and iPSCs can be differentiated into keratinocytes. However, these keratinocytes exhibit an epidermal squamous cell phenotype and thus do not have the capacity to regenerate hair follicles. To date, no successful protocols have been developed to make human hair follicles. Human hair follicle epithelial stem cells have been characterized and they express markers such as K15 or CD200. However, these cells can not be cultured or expanded in vitro because these stem cells rapidly lose stem cell marker expression and function in vitro.

SUMMARY OF THE INVENTION

In accordance with the present invention, a strategy for differentiating human induced pluripotent stem cells (hiPSCs) into CD200+/ITGA6+ EpSCs that can reconstitute the epithelial components of hair follicles and interfollicular epidermis is disclosed. The hiPSC-derived CD200+/ITGA6+ cells have high colony forming efficiency and show a similar gene expression signature as that of EpSCs isolated directly from human hair follicles. In skin reconstitution assays, hiPSC-derived CD200+/ITGA6+ cells combined with neonatal mouse dermal cells injected into or grafted onto an immunodeficient mouse produce all hair follicle lineages including hair shaft, inner and outer root sheaths. The regenerated hair follicles consist of a KRT15+ stemcell population and in situ hybridization confirms that the follicular epithelium and interfollicular epidermis are composed entirely of human keratinocytes.

Our results indicate that hiPSC-derived CD200+/ITGA6+ cells are molecularly and functionally similar to human hair follicle-derived EpSCs. These results suggest that a sufficient number of folliculogenic hEpSCs can be generated from hiPSCs to develop treatments for hair loss, wounds and other degenerative skin disorders.

BRIEF DESCRIPTION OF THE DRAWINGS

The application file contains at least one drawing executed in color. Copies of this application with color drawings will be provided by the Patent and Trademark Office upon request and payment of the necessary fee.

FIG. 1A-FIG. 1C. Characterization of hiPSCs derived from primary human fibroblasts. FIG. 1A-FIG. 1B shows morphology of hiPSCs. hiPSCs exhibit hESC-like morphology in co-culture with mouse embryonic feeder fibroblasts (a); AP staining of hiPSCs (b); Scale bars: left panel, 200 IJm; right panel, 50 μm. FIG. 1C—As shown via immunocytochemistry, hiPSC clones express markers common to pluripotent cells, including OCT3/4, NANOG, SSEA3, SSEA4 and TRA-1-60. 4,6-Diamidino-2-phenylindole (DAPI) staining indicates cell nuclear. Scale bar, 30 μm FIG. 2. Gene expression in hiPSCs is similar to hESCs. qPCR assay for expression of OCT3/4(endo), SOX2(endo), NANOG, TERT, KLF4(endo) and REX1 in hESCs, hiPSCs and parental fibroblasts (hFs). Individual PCR reactions were normalized against internal controls (3-actin).

FIG. 4A shows analysis of DNA methylation and histone modification in the OCT3/4 and NANOG promoters in the hiPSCs, hESCs and hFs. Bisulfite genomic sequencing of the promoter regions of OCT3/4 and NANOG in 10 randomly selected hiPSC and hESC clones, as well as human fibroblasts (hFs). Open circles indicate unmethylated CpG dinucleotides, whereas closed circles indicate methylated CpGs. FIG. 4B shows chromatin immunoprecipitation was performed using antibodies against dimethylated histone H3K4 (H3K4me2) and H3 acetylation (acH3). OCT3/4 and NANOG promoters showed enrichment for the active (H3K4me2 and acH3) mark in hiPSCs, similar to hESCs. In hFs, OCT3/4 and NANOG promoters appeared in the inactive state.

FIG. 7A-FIG. 7B. Flow cytometric analysis of the percentage of CD200+/ITGA6+(FIG. 7A) and SSEA3+(FIG. 7B) cell populations at day 11, 18 and 25 when iPSCs were induced by BMP4 only.

FIG. 8. Flow cytometric analysis of staged expression of CD200 and ITGA6 when EGF was added at day 2 during the differentiation. Flow cytometric analysis was performed using antibodie specific for CD200 and ITGA6. CD200+/ITGA6+ cell percentage was monitored at 11, 18 and 25 days respectively.

FIG. 10A-FIG. 10I. Differentiation of hiPSCs into human EpSCs. FIG. 10A shows an outline of the protocol used to differentiate hiPSCs to EpSCs and more mature keratinocytes. FIG. 10B shows a morphology of hiPSCs, hiPSC-derived EpSCs (hiPSC-EpSCs) and hiPSC-derived mature keratinocytes (hiPSC-keratinocytes). FIG. 10C-FIG. 10E shows a flow cytometric analysis of CD200+/ITGA6+, KRT15+ and KRT14+ cells at day 0 and 18 during the differentiation. FIG. 10E-FIG. 10H shows a statistical analysis of CD200+/ITGA6+, KRT15+ and KRT14+ cells obtained by flow cytometric analysis. Data shown are mean±SD of cell percentage from three independent experiments. FIG. 10I shows a qPCR analysis of OCT3/4, NANOG, KRT5, KRT8, KRT14, KRT15, LamB3, involucrin and flaggrin in hiPSC-derived cells at different stages of differentiation. Data shown are mean±SD of cell percentage from three independent experiments.

FIG. 11A-FIG. 11J. Molecular characterization of hiPSCs-derived EpSCs. FIG. 11A shows representative dishes of isolated normal skin-derived keratinocytes(Normal skin keratinocytes), hiPSC-derived CD200+/ITGA6+ cells (hiPSC-derived EpSCs or hiPSC-EpSCs), hiPSC-derived CD200-/ITGA6+ cells, and hiPSC-keratinocytes cultured for 3 weeks on 3T3 fibroblast feeder cells. FIG. 11B shows qPCR analysis of known EpSC markers, including LGR5, LGR6, CD200, KRT15, ITGA6, TCF4, FZD2, DKK3, CTNNB1, LEF1 and LHX2 as well as keratinocyte markers KRT14 and KRT8 in hiPSC-EpSCs, CD200+/ITGA6+ cells isolated from fetal hair follicles (hEpSCs) and parental hiPSCs. Expression of these genes in hiPSC-EpSCs is similar to hEpSCs isolated directly from fetal scalp hair follicles. FIG. 11C-FIG. 11F shows imunnocytochemical analysis of KRT15, KRT1, KRT10 and ITGB1 in hiPSC-EpSCs and hEpSCs culture. Secondary antibodies are conjugated by FITC. Antibody against ITGB1 is conjugated by PE. Scale bar, 50 μm. FIG. 11G shows hierarchical clustering among the three cell populations analyzed. FIG. 11H shows heat-map of genes differentially expressed in RNA-microarray analysis performed on hiPSCs, hiPSC-EpSCs and hEpSCs. FIG. 11I-FIG. 11J shows scatter plots show that keratinocyte markers are expressed in hiPSC-EpSCs, whereas iPSCs markers are silenced.

FIG. 21A-FIG. 21J. Multipotency of hiPSC-derived EpSCs in vivo. FIG. 21A shows hair follicles form from hiPSC-derived CD200+/ITGA6+/SSEA− cells injected into the skin of an immunodeficient mouse in combination with mouse neonatal dermal cells. After 3 weeks, grafts were photographed in regular and human hair follicles were observed. Dotted short lines outline a hair follicle. Arrowhead points to pigmented bulb region of hair follicle. FIG. 21B shows H&E staining of a cyst with hair follicles formed from hiPSC-EpSCs. An arrowhead points to a hair follicle. FIG. 21C shows Human specific Alu probe staining (green nuclei) which confirms human origin of follicular epithelium and epidermal cyst lining which were generated by hiPSC-derived EpSCs. An arrowhead points to a hair follicle. Scale bar, 200 μm. FIG. 21D-FIG. 21E shows in situ hybridization using pan-centromeric probes specific for human (red) and mouse (green) respectively show human origin of follicular epithelium (d) and epidermal cyst lining (e). Scale bar, 30 μm. FIG. 21F shows hair follicles formed from hiPSC-derived CD200+/ITGA6+/SSEA− cells mixed with mouse neonatal dermal cells in the chamber. FIG. 21G shows H&E staining of hair follicles in the graft using chamber assay. iPSC-EpSCs and mouse neonatal fibroblast were mixed together in a chamber and subjected to the back skin of mouse. After three weeks, hair follicles with hair shaft structure formed on the graft were stained by H&E and photographed. Scale Bar, 150 um. FIG. 21H shows human like multilayered skin generated in the chamber graft was stained by H&E. Scale Bar, 150 um. FIG. 21I-FIG. 21J shows human specific Alu probe staining of human hair follicles(h) and epidermis(j) in the chamber graft. Human cells were stained by human specific Alu probe labeled with FITC. Scale Bar, 150 um.

FIG. 22A-FIG. 22B. Flow cytometric analysis of the percentage of CD200+ and KRT15+ cells in the neonatal foreskin-derived keratinocytes and hiPSC-derived keratinocytes (FIG. 22A). QPCR analysis of the expression of epithelial marekers among hiPSCs, hEpSCs, hiPSCEpSCs, hiPSC-derived keratinocytes(hiPSC-keratinocytes) and neonatal foreskin-derived keratinocytes (Foreskin-keratinocytes) (FIG. 22B).

FIG. 23. In the skin permeability assay, the multilayered skin in the chamber graft is permeable to toluidine blue. Human-like skin in the chamber graft was treated with toluidine blue dissolved in OMSO (up panel) and H₂O (down panel) respectively. Human-like skin was impermeable to toluidine blue dissolved in H₂O. Toluidine blue dissolved OMSO permeated into skin and skin was dyed in blue.

FIG. 24A-FIG. 24G. FIG. 24A-FIG. 24B show immunostaining of reconstituted hair follicles formed by neonatal foreskin-derived keratinocytes or hiPSC-EpSCs with antibody against KRT15 (a) or KRT14 (b), respectively. Scale bar, 50 µm. hiPSC-hair follicle represents the hair follicle derived from hiPSC-EpSCs. FK-hair follicle represents the hair follicle derived from neonatal foreskin-derived keratinocytes. FIG. 24C-FIG. 24E show immunostaining of hair follicles formed from hiPSC-EpSCs using hair differentiation markers AE13 (c), AE15 (d) and K75(e). Arrowheads point to the positive areas. Scar bar, 100 µm. FIG. 24F-FIG. 24G shows KRT10 and Involucrin were expressed in the interfollicular epidermis. Scale Bar, 50 µm. Immunochemistry was performed with antibodies against KRR10 and Involucrin.

FIG. 25A-FIG. 25B. Original immunostaing results of AE13 (FIG. 25A) and AE15 (FIG. 25B) in the hiPSC-derived hair follicle, which are illustrated in FIG. 4C and FIG. 4D.

FIG. 26. Original immunostaing results of K75 in the hiPSC-derived hair follicle, which are illustrated in FIG. 4e.

FIG. 27A-FIG. 27B. Oil red staining of sebocyte and qPCR analysis of sebocyte markers. FIG. 27A shows sebocytes derived from iPSC-EpSCs were stained with Oil and showed Oil positive. FIG. 27B shows qPCR analysis of sebocyte markers, including KRT7, PPAR-a and LPL in hEpSCs, hEpSCs, hiPSC-Sebocytes and HaCaT-Sebocytes.

FIG. 28. Flow cytometric analysis of iPSC-derived keratinocytes. CD200+/ITGA6+ and CD200−/ITGA6+ cells were culture in another 25 days and flow cytometric analysis was performed to detect the cell percentage of the expression of KRT14.

DETAILED DESCRIPTION OF THE INVENTION

Figure 2:
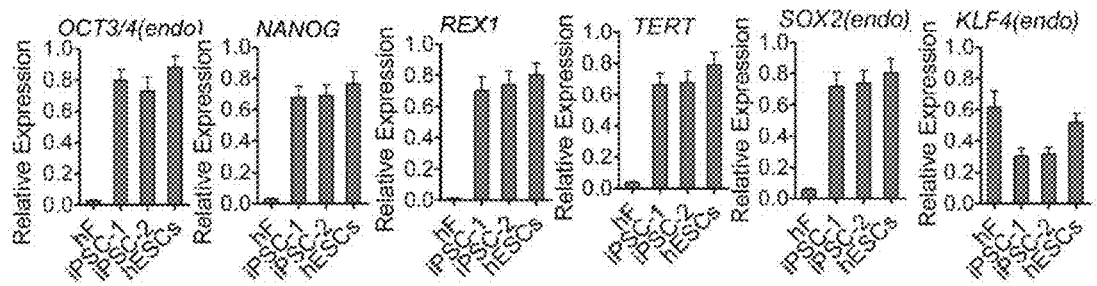

In accordance with the present invention, methods have been developed for differentiating human iPSCs into epithelium stem cells and mature squamous cells. Methods employing such cells for producing hair follicles are also disclosed. We generated iPSCs from human dermal fibroblasts using retroviral vectors encoding four reprogramming factors (namely Oct3/4, Sox2, KIf4, and c-Myc). The reprogrammed cells exhibit all the features associated with iPSCs. They were cultured in a growth factor defined medium. Cells with morphological features of keratinocytes appeared after 7 days and keratinocyte colonies were well formed in 11 days. These colonies were collected and tested for epithelial stem cell marker expression. A subpopulation of cells expressing CD200, K15, alpha6 integrin, CD34, and K14 were analyzed using FACS.

Definitions

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein, the term "growth factor" refers to a protein, peptide or other molecule having a proliferative, viability, division arrest, or differentiation effect on any cell type present in the cell system under consideration. Growth factors that can be used include any trophic factor that promotes stem cells to proliferate, including any molecule that binds to a receptor on the surface of the cell to exert a proliferative effect on the cell. Preferred proliferation-inducing growth factors include EGF, amphiregulin, acidic fibroblast growth factor (aFGF or FGF-1), basic fibroblast growth factor (bFGF or FGF-2), transforming growth factor alpha (TGFalpha.), and combinations thereof. Growth factors are usually added to the culture medium at concentrations ranging between about 1 ng/ml to 10 µg/ml. Concentrations about between 1 to 100 ng/ml are usually sufficient. Titration experiments can be performed to determine the optimal concentration of a particular growth factor.

In addition to proliferation-inducing growth factors, other growth factors can be added to the culture medium that influence viability and differentiation of the cells including NGF, platelet-derived growth factor (PDGF), thyrotropin releasing hormone (TRH), transforming growth factor betas (TGF-beta), insulin-like growth factor (IGF-1) and the like.

The term "isolated" as used herein signifies that the cells are placed into conditions other than their natural environment. The term "isolated" does not preclude the later use of these cells thereafter in combinations or mixtures with other cells.

As used herein, the term "expanding" refers to increasing the number of like cells through symmetrical cell division (mitosis). The term "proliferating" and "expanding" are used interchangeably.

The term "reprogramming" as used herein refers to a process that reverts a cell from a late developmental stage of phenotypic restriction (i.e., differentiated) to an earlier developmental stage of phenotypic potential (i.e., undifferentiated) at which a greater number of phenotypic lineages are available to progeny cells. In one embodiment, when complete, reprogramming yields iPSCs that have the ability to produce progeny cells inclusive of the full range of possible developmental phenotypes. In another embodiment, the reprogramming may be incomplete or partial, yielding less differentiated cells that can recapitulate only a subset of the full range of developmental phenotypes, but still many more than were available before the reprogramming. In one embodiment, reprogramming refers to a process of driving the differentiation of a cell backwards to a more undifferentiated or more primitive type of cells. In some embodiment, reprogramming encompasses reversion of differentiation state of a differentiated cell, (e.g., a somatic stem cell) to a pluripotent state.

In some embodiments, reprogramming of a differentiated cell (e.g., a somatic cell or tissue stem cell) causes the differentiated cell to assume a pluripotent-like state. The resulting cells are referred to herein as "reprogrammed cells" or "undifferentiated cells".

Reprogramming involves alteration, e.g., reversal, of at least some of the heritable patterns of nucleic acid modification (e.g., methylation), chromatin condensation, epigenetic changes, and genomic imprinting, etc., that occur during cellular differentiation as a zygote develops into an adult, the result being a change from a differentiated to an undifferentiated state. Reprogramming is distinct from simply maintaining the existing undifferentiated state of a cell that is already pluripotent or maintaining the existing less than fully differentiated state of a cell that is already a multipotent cell (e.g., a hematopoietic stem cell). Reprogramming is also distinct from promoting the self-renewal or proliferation of cells that are already pluripotent or multipotent, although the compositions used in methods of the invention (e.g. xanthine) may also be of use for such purposes. The methods of the present invention contribute to establishing the pluripotent state. The methods can be practiced on cells that are fully differentiated and/or restricted to giving rise only to cells of that particular type, rather than on cells that are already multipotent or pluripotent.

The term "reprogrammed cell" as used herein refers to a cell which has been reprogrammed from a differentiated cell according to the methods as disclosed herein, for example reprogrammed to a pluripotent state, a multipotent state, or a more undifferentiated state than the originally treated cell. The term "reprogrammed cell" encompasses an undifferentiated cell compared to the stage of differentiation of the starting treated cell.

In one embodiment, the reprogrammed cell has not been completely reprogrammed to a pluripotent state but rather to a non-pluripotent stable intermediate state, e.g., a cell that can differentiate into one or two of three germ layers, but cannot differentiate into all three of the germ layers. In some embodiments, the reprogrammed cell expresses at least one or at least two or at least three but not all of the following markers; alkaline phosphatase (AP), NANOG, OCT-4, SOX-2, SSEA4, TRA-1-60 or TRA-1-81. In some embodiments, the reprogrammed cell expresses markers from one or two germ cell layers, but not markers from all three embryonic germ layers (i.e. a partially reprogrammed cell does not express markers from all three layers of endoderm, mesoderm or ectoderm layers). Markers of endoderm cells include, Gata4, FoxA2, PDX1, Nodal, Sox7 and Sox17. Markers of mesoderm cells include, Brachycury, GSC, LEF1, Mox1 and Tie1. Markers of ectoderm cells include criptol, $EN^1$, GFAP, Islet 1, LIM1 and Nestin. In some embodiments, the reprogrammed cell is an undifferentiated cell.

The term "contacting" or "contact" as used herein as in connection with contacting a differentiated cell (e.g. tissue stem cell) with a compound as disclosed herein (e.g., an expression vector), includes subjecting the cell to a culture media, which comprises the compound. Where the differentiated cell is in vivo, contacting the differentiated cell with a compound includes administering the compound in a composition to a subject via an appropriate administration route such that the compound contacts the differentiated cell in vivo.

The term "pluripotent" when used in reference to a "pluripotent cell" refers to a cell with the capacity, under different conditions, to differentiate to cell types characteristic of all three germ cell layers (endoderm, mesoderm and ectoderm). Pluripotent cells are characterized primarily by their ability to differentiate to all three germ layers, using, for example, a nude mouse teratoma formation assay. Pluripotency is also evidenced by the expression of embryonic stem (ES) cell markers, although a preferred test for pluripotency is the demonstration of the capacity to differentiate into cells of each of the three germ layers. In some embodiments, a pluripotent cell is an undifferentiated cell.

The term "pluripotency" or a "pluripotent state" as used herein refers to a pluripotent cell with the ability to differentiate into all three embryonic germ layers: endoderm (gut tissue), mesoderm (including blood, muscle, and vessels), and ectoderm (such as skin and nerve), and typically has the potential to divide in vitro for a long period of time, e.g., greater than one year or more than 30 passages.

The term "multipotent" when used in reference to a "multipotent cell" refers to a cell that is able to differentiate into some but not all of the cells derived from all three germ layers; or multiple cell types that constitute a single type of tissue or organ. Thus, a multipotent cell is a partially differentiated cell. Multipotent cells are well known in the art, and examples of multipotent cells include tissue stem cells, such as for example, hematopoietic stem cells and neural stem cells, hair follicle stem cells, liver stem cells etc. Multipotent means a stem cell can form many types of cells in a given lineage, but not cells of other lineages. For example, a multipotent blood stem cell can form the many different types of blood cells (red, white, platelets, etc.), but it cannot form neurons; cardiovascular progenitor cell (MICP) differentiate into specific mature cardiac, pacemaker, smooth muscle, and endothelial cell types; pancreas-derived multipotent progenitor (PMP) colonies produce cell types of pancreatic lineage (cells that produces insulin, glucagon, amylase or somatostatin) and neural lineage (cells that are morphologically neuron-like, astrocytes-like or oligodendrocyte-like).

The term "multipotency" refers to a cell with the degree of developmental potential that is less than totipotent and pluripotent.

The term "totipotency" refers to a cell with the developmental capacity to yield all of the cells in the adult body as well as the extra-embryonic tissues including the placenta. The fertilized egg (zygote) is totipotent as are the early cleaved cells (blastomeres)

The term "differentiated cell" means any cell that does not have stem cell capacity, where stem cell capacity is the ability to divide in a manner that renews a baseline state of relative undifferentiation (stem cell phenotype) will simultaneously producing cells of different and developmentally more restricted state of differentiation (i.e. differentiated non-stem cells). In practice, the terms differentiated and undifferentiated always require a developmental reference, whether explicit or implicit. Tissue stem cells are undifferentiated relative to their differentiated, non-stem progeny cells. However, relative to iPSCs, embryonic stem cells, and embryonic precursor cells, tissue stem cells are more differentiated. It should be noted that placing many primary cells in culture can lead to some loss of fully differentiated characteristics. Thus, simply culturing such cells are included in the term differentiated cells and do not render these cells tissue stem cells or pluripotent cells. The transition of a differentiated cell to pluripotency requires a reprogramming stimulus beyond the factors that lead to partial loss of differentiated character in culture. Reprogrammed cells also have the characteristic of the capacity of extended passaging without loss of proliferative potential, relative to their primary cell parents, which generally have capacity for only a limited number of divisions in culture.

As used herein, the term "somatic cell" refers to any cell other than a germ cell, a cell present in or obtained from a pre-implantation embryo, or a cell resulting from proliferation of such a cell in vitro. Stated another way, a somatic cell refers to any cells forming the body of an organism, as opposed to germ line cells. In mammals, germ line cells (also known as "gametes") are the spermatozoa and ova, which fuse during fertilization to produce a cell called a zygote, from which the entire mammalian embryo develops. Every other cell type in the mammalian body (aside from the sperm and ova), is a somatic cell: internal organs, skin, bones, blood, and connective tissue are all made up of somatic cells. In some embodiments the somatic cell is a "non-embryonic somatic cell", by which is meant a somatic cell that is not present in or obtained from an embryo and does not result from proliferation of such a cell in vitro. In some embodiments, the somatic cell is an "adult somatic cell", by which is meant a cell that is present in or obtained from an organism other than an embryo or a fetus or results from proliferation of such a cell in vitro. Unless otherwise indicated the methods for reprogramming a differentiated cell can be performed both in vivo and in vitro (where in vivo is practiced when a differentiated cell is present within a subject, and where in vitro is practiced using isolated differentiated cell maintained in culture). In some embodiments, where a differentiated cell or population of differentiated cells are cultured in vitro, the differentiated cell can be cultured in an organotypic slice culture, such as described in, e.g., Meneghel-Rozzo et al., 2004, Cell Tissue Res, 316: 295-303, which is incorporated herein in its entirety by reference.

As used herein, the term "adult cell" refers to a cell found throughout the body after embryonic development.

As used herein, the terms "iPS cell" and "induced pluripotent stem cell" are used interchangeably and refers to a pluripotent cell technically derived (e.g., induced by complete or partial reversal) from a differentiated cell (e.g. a non-pluripotent cell), typically an adult differentiated cell.

The term "progenitor cell" is used herein to refer to cells that have a cellular phenotype that is at an earlier step along a developmental pathway or progression than is a later differentiated cell relative to a cell to which it can give rise by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate. Progenitor cells are distinct from tissue stem cells in that they lack asymmetric self-renewal. In the absence of their own producer stem cell, progenitor cells' populations are rapidly exhausted because of their inability to simultaneously preserve their own initial degree of differentiation.

In the context of cell ontogeny, the term "differentiate", or "differentiating" is a relative term meaning a "differentiated cell" is a cell that has progressed further down the developmental pathway than its precursor cell. Thus, in some embodiments, a reprogrammed cell as this term is defined herein, can differentiate to lineage-restricted precursor cells (such as a mesodermal stem cell or a endodermal stem cell), which in turn can differentiate into other types of precursor cells further down the pathway (such as a tissue specific precursor, for example, a cardiomyocyte precursor, or a pancreatic precursor), and then to an end-stage differentiated cell, which plays a characteristic role in a certain tissue type, and may or may not retain the capacity to proliferate further.

The term a "reprogramming gene", as used herein, refers to a gene whose expression, contributes to the reprogramming of a differentiated cell, e.g., a mature differentiated cell to an undifferentiated cell that maintains a pluripotent state or partially pluripotent state. A reprogramming gene can be, for example, genes encoding master transcription factors Sox2, Oct3/4, Klf4, Nanog, Lin-38, c-myc and the like.

The term "exogenous" refers to a substance present in a cell that was introduced from outside the cell by either a natural process or via genetic recombination. The terms "exogenous" when used herein refers to a nucleic acid (e.g., a nucleic acid encoding a reprogramming transcription factor, e.g., SOX2, OCT3/4, KLF4, NANOG, LIN-38, c-MYC and the like) or a protein (e.g., a transcription factor polypeptide) that has been introduced by a process involving the hand of man into a biological system such as a cell or organism in which it is not normally found or in which it is found in lower amounts. A substance (e.g. a nucleic acid encoding a SOX2 transcription factor, or a protein, e.g., a SOX2 polypeptide) will be considered exogenous if it is introduced into a cell or an ancestor of the cell that inherits the substance. In contrast, the term "endogenous" refers to a substance that is produced within the cell by natural processes.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

The following materials and methods are provided to facilitate the practice of the present invention.

Cell Culture

Human primary fibroblasts were obtained from discarded normal skin after surgery following a protocol approved by the University of Pennsylvania Institutional Review Board. HEK 293T cells and human fibroblasts were cultured in DMEM supplemented with 10% fetal bovine serum (FBS), 2 mM L-glutamine, 100 unit/ml penicillin and 100 µg/ml of streptomycin (all from Invitrogen). hiPSCs were cultured on MEF feeders using hESC which contains 80% DMEM/F12 (1:1) medium, 20% knockout Serum Replacement, 100 uM non-essential amino acids, 2 mM L-glutamine, 0.1 mM β-mercaptoethanol, 100 unit/ml penicillin, 100 µg/ml streptomycin and 10-15 ng/ml bFGF (all from Invitrogen).

hiPSC Generation with Retroviral Infection

To prepare the retroviruses, HEK 293T cells were transfected with pMXs plasmids containing the coding sequences for SOX2, OCT3/4, and KLF4, along with pUMVC and pCMV-VSV-G plasmids at the ratio of 10 ug of plasmid DNA to 20 µl of Fugene 6 (Roche) in 500 µl Opi-MEM (Invitrogen). The ratio of pMXs:pUMVC:pCMV-VSV-G was 3:2:1. The next day the culture media containing the retroviruses was harvested and concentrated by Retro-X™ Concentrator (TAKARA). The human fibroblasts were plated at $1 \times 10^5$ cells per well in 6-well plates one day before infection with the retroviruses. The retrovirus solution was added to the fibroblasts and incubated overnight. 24 hours after the infection, infected fibroblasts were plated in gelatin-coated 100 mm dishes containing irradiated feeder cells. One day after plating on feeder cells, the media was changed to hiPSC media. hESC-like clones were observed 25-30 days after the initial infection. The hiPSC clones were picked up around 45 days after the initial infection. 8 lines of hiPSC were established and used in the subsequent experiments.

Characterization of hiPSCs

The RT-PCR analyses, alkaline phosphatase staining, teratoma formation, bisulphite genomic sequencing and histone modification experiments were performed as previously described (15, 17, 37). The primers used for RT-PCR are listed in Supplementary Table 1.

Differentiation of hiPSCs into CD200+/ITGA6+ Cells and Keratinocytes

Prior to differentiation, the cells were feeder depleted by culturing on a thin layer of matrigel (BD Biosciences) in hESC media for 24 to 48 hours. For differentiation, cells were dissociated to small clusters (10-20 cells) with collagenase IV (1 mg/ml, Invitrogen) for 20 min followed by trypsin-EDTA (0.05%) for approximately 2 min. The clusters were washed and cultured in 6-well low-cluster plates (Corning) in 2 ml hESC media containing Y27632 without bFGF to form embryoid bodies (EBs). EBs were seeded onto mitomycin-C-treated 3T3 fibroblasts in differentiation media. Cells were grown in the differentiation medium until clones of epithelial cells were observed and isolated around 11 days. The epithelial cells were plated and cultured on 3T3 fibroblasts again until the population of CD200+/ITGA6+ cells reached to maximum level around 18 days. The CD200+/ITGA6+ cells were sorted out and cultured in the differentiation media containing EGF. The characteristic mature keratinocytes were obtained by 40 days after the differentiation. For differentiation to the epithelial lineage, the following molecules were used: days 0-1, BMP4 (1 ng/ml, R&D system); days 1-11, all-trans RA (1 µM, Sigma-Aldrich); days 3-11, BMP4 (25 ng/ml), EGF (20 ng/ml, R&D system); days 11-25, BMP4 (1 ng/ml), EGF (20 ng/ml); days 25-, EGF (20 ng/ml). Initiation medium (3:1 mixture of DMEM and Ham's F12 media with 2% FBS, 5 µg/ml insulin, 0.5 µg/ml hydrocortisone, 10-10 mol/l cholera toxin, 1.37 ng/ml triiodothyronine, 0.3 mmol/l L-ascorbic acid and 24 µg/ml adenine) was used at day 1-7. Induced medium 1 (Defined Keratinocyte-SFM (Invitrogen) with 5 µg/ml insulin, 0.2 µg/ml hydrocortisone, 10-10 mol/l cholera toxin, 1.37 ng/ml triiodothyronine, 0.3 mmol/l L-ascorbic and 10 µg/ml adenine) was used at day 8-11. Induced medium 2 (1:1 mixture of Keratinocyte-SFM (Invitrogen) and Defined Keratinocyte-SFM) was used at day 11-25. Induced medium 3 (Keratinocyte-SFM) was used at day 25-.

Flow Cytometry and Cell Sorting

Cells were stained at a concentration of $2.5 \times 10^6$ cells/ml with antibody against CD200, ITGA6, SSEA3, KRT14 and KRT15. For cell-surface markers, staining was carried out in PBS with 2% FBS. For intracellular proteins, staining was carried out on cells fixed with 4% paraformaldehyde (Electron Microscopy Sciences) in PBS. Staining was done in PBS with 2% FBS. Stained cells were analyzed using an LSRII flow cytometer (BD Biosciences). For Fluorescence Activated Cell Sorting, the cells were sorted at a concentration of $10^6$ cells/ml in PBS/2% FBS using a FACS Aria™II cell sorter (BD Biosciences). For magnetic bead sorting, the Miltenyi MACS bead sorting system was used according to the manufacturer's guidelines and sorting conditions. Data were analyzed using FlowJo software (Treestar). A comprehensive list of antibodies is described in Supplementary Table 2.

Patch Assay

Skin reconstitution assay was performed as described previously (27, 28). In brief, hiPSC-derived CD200+/ITGA6+/SSEA3− cells were isolated and combined with freshly isolated dermal cells from neonatal mice. In all experiments, approximately equal numbers of epithelial and dermal cells (1 million each) were combined at a concentration of $10^4$/ul cells in DMEM/F12 and injected subcutaneously into immune-compromised NU/NU Nude mouse. Two and a half weeks after implantation, the mice were killed and the subcutaneous growths were dissected, and processed for histology and immunohistochemistry. Immunohistochemistry was performed as previously described (37). A comprehensive list of antibodies is provided as Supplementary Table 2. Appropriate Alexa488 or Alexa590—conjugated secondary antibodies (Molecular Probes) were used with 4',6-diamidino-2-phenylindole (DAPI) nuclear counterstain (Vector lab).

Chamber Assay

The cellular grafting procedure for hair follicle reconstitution in vivo was performed as described previously (32, 38). Briefly, hiPSC-derived EpSCs and mouse neonatal dermal cells (5 million each) were resuspended individually or mixed together in the medium, and were then transferred to grafting chambers implanted on the back skins of immune-compromised NU/NU Nude mouse. The chambers were removed 1 week after grafting, and hair follicle formation was assessed at 3-4 weeks. Part of each grafting site was dissected for histological observation.

Global Gene Profiling and Array Analysis

Micro-array raw data generated from Illumina Chip were normalized, background-corrected, and summarized using the R package "lumi" 39. To reduce false positives, the unexpressed probes were removed, leaving 21,758 probes that were examined in all experiments described herein. The R package "limma" (40, 41) was employed for gene differentially expression analysis, followed by multiple test correction by the Benjamini and Hochberg procedure (42). The genes with the adjusted p values<0.05 and fold change>4 were subjected to the two-way clustering analysis for generating the heat map.

In Situ Hybridization

Briefly, paraffin slides were dehydrated, antigen retrieved, and hybridized with Alu DNA probe (BioGenex): heat slide to 85° C. 10 min, and then 37° C. overnight. The slides were then incubated with antibody specific for fluorescein, biotin-labeled (BioGenex), and finally incubated with secondary antibody labeled with Streptavidin-Alexa Fluo488. DAPI was used to label the nuclear DNA.

The following example is provided to illustrate certain embodiments of the invention. It is not intended to limit the invention in any way.

Example 1

Generation of Human Epithelial Stem Cells

Figure 3:
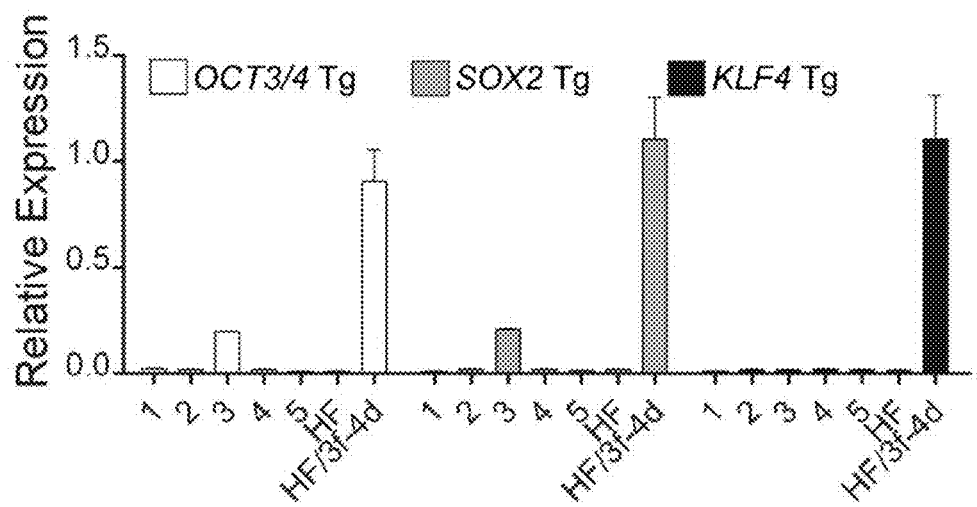
FIG. 3. qPCR analysis of retroviral transgene expression in the hiPSC clones. Transgene-specific PCR primers permit determination of the relative retrovirally expressed (transgene) genes (OCT3/4, SOX2 and KLF4) via qPCR. Tg represents transgene. Five different hiPSC clones were tested. hF stands for human fibroblasts and hF/3f-4d stands for human fibroblasts 4 days after virally infection with OCT3/4, SOX2 and KLF4.
Figure 4A:
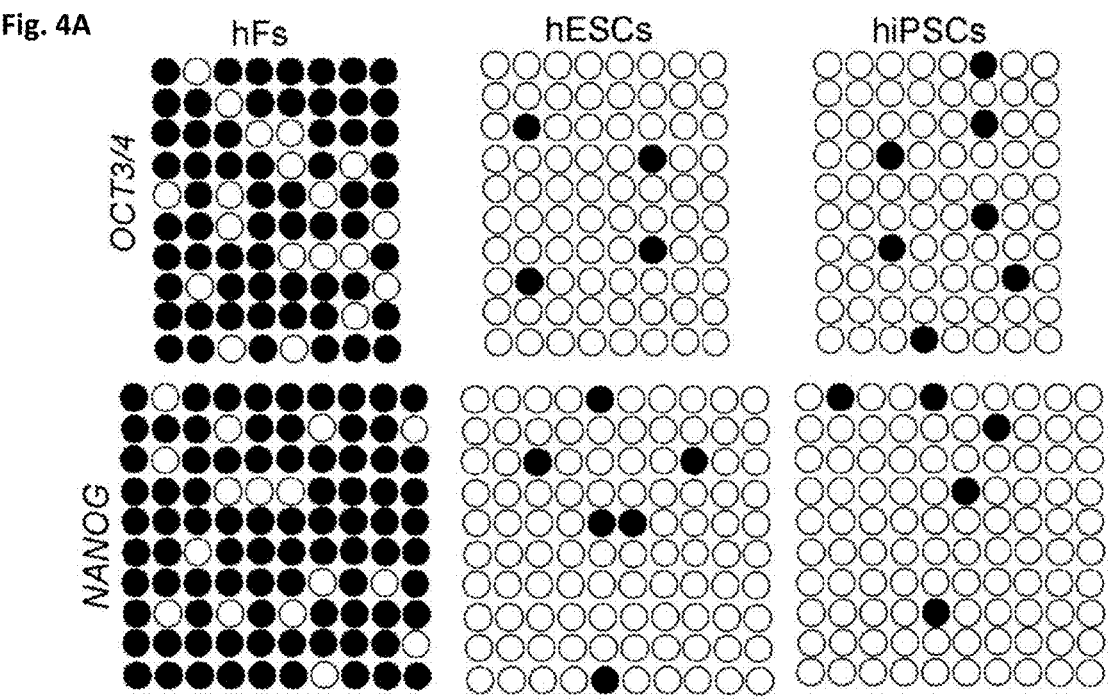
FIG. 4A-FIG. 4B.
Figure 4B:
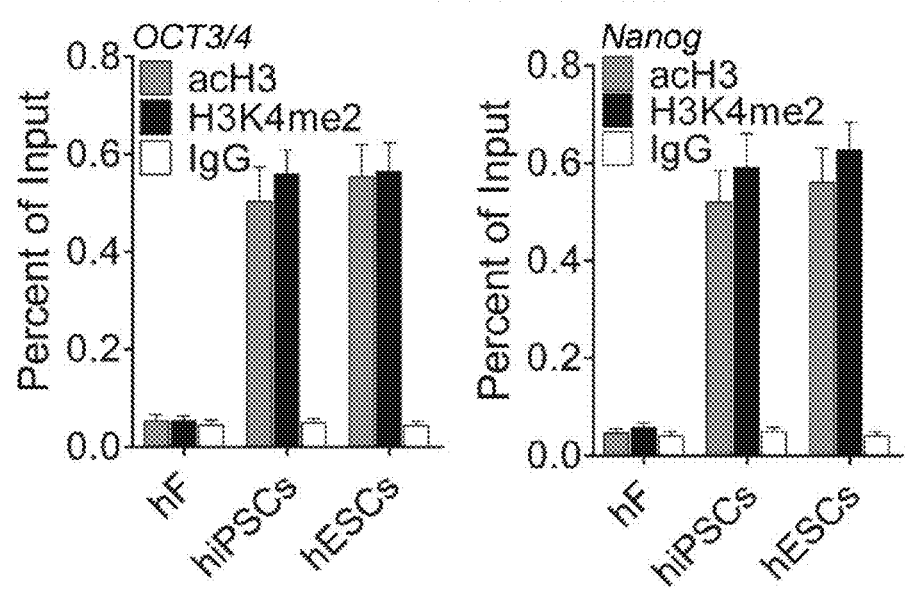
Figure 5:
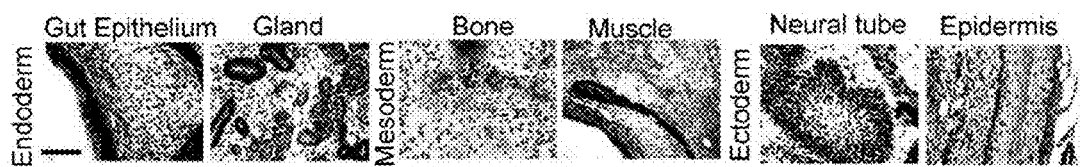
FIG. 5. Pluripotent characterization of hiPSCs. hiPSCs were injected into immunodeficient mouse and generated well-differentiated teratoma-like masses containing all three embryonic germ layers (endoderm, mesoderm and ectoderm). Scale bar, 50 μm.

We generated hiPSCs from freshly isolated dermal fibroblasts using OCT3/4, SOX2 and KLF4 as previously described[14-17]. hiPSC clones exhibiting characteristic human embryonic stem cell (hESC) morphology were isolated around 45 days after transduction (FIG. 1A). Similar to the H9 hESCs, our hiPSC lines showed high levels of alkaline phosphatase (also known as TRA2-49-6E) activity (FIG. 1B) and expressed multiple pluripotency markers[15, 17], including nuclear transcription factors OCT3/4 and NANOG as well as surface antigens SSEA3, SSEA4 and TRA-1-60 (FIG. 1C). While a series of endogenous stemness genes, including POU class 5 homeobox 1(OCT3/4), nanog homeobox (NANOG), SRY (sex determining region Y)-box 2 (SOX2), REX1 and telomerase reverse transcriptase (TERT), were activated in hiPSCs, as revealed by quantitative real time PCR (qPCR) (FIG. 2), the three retroviral transgenes were silenced (FIG. 3). Compared with the parental fibroblasts, hiPSCs displayed extensive demethylation of CpG dinucleotides in the OCT3/4 and NANOG promoters, as shown by bisulphite sequencing (FIG. 4A). We also found that histone H3 lysine 4 was methylated and histone H3 was acetylated in the promoter regions of OCT3/4 and NANOG in hiPSCs (FIG. 4B). Pluripotency of the hiPSC clones was confirmed in teratoma formation assays after injection of undifferentiated hiPSCs into immunocompromised NOD/SCID mice (FIG. 5).

Figure 6:
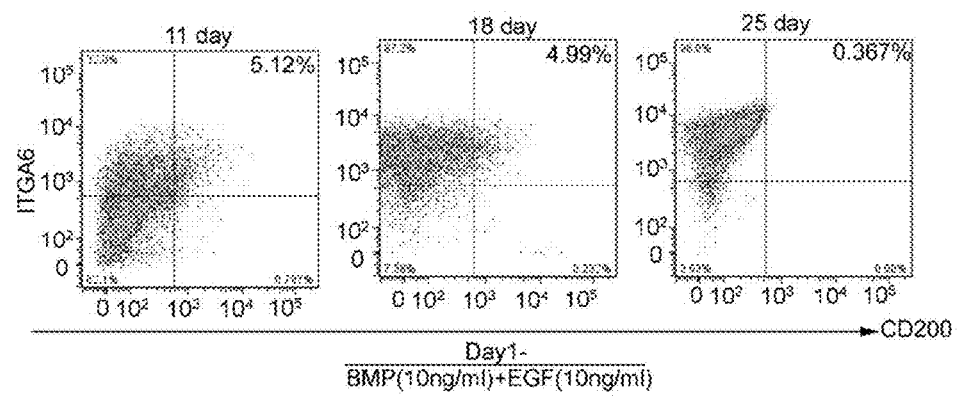
FIG. 6. Flow cytometric analysis of staged expression of CD200 and ITGA6 when EGF was added at day 1 during the differentiation. Flow cytometric analysis was performed using antibody specific for CD200 and ITGA6. D200+/ITGA6+ cell percentage was monitored at 11, 18 and 25 days respectively.
Figure 9:
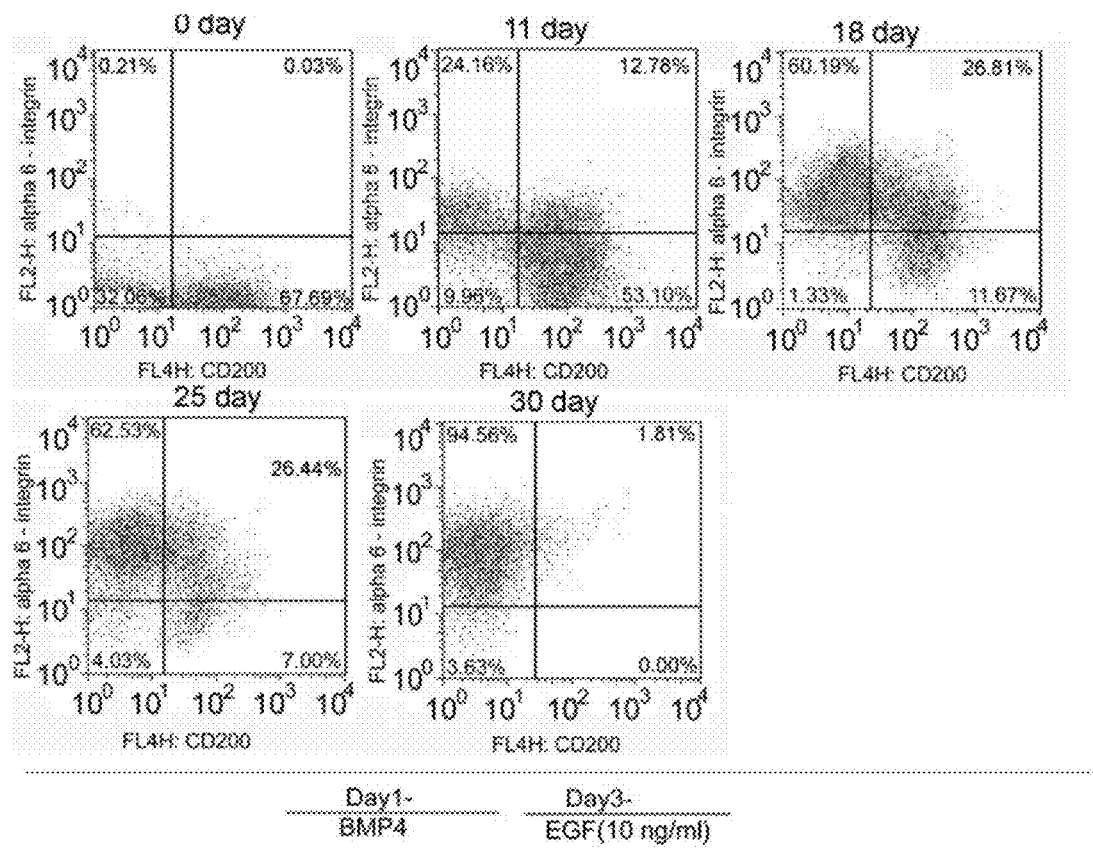
FIG. 9. Flow cytometric analysis of positive cells for CD200 and ITGA6 during keratinocyte differentiation from hiPSCs. Flow cytometric analysis was performed using antibodies specific for CD200 and ITGA6. CD200+/ITGA6+ cell percentage was monitored at 0, 11, 18, 25 and 30 days respectively.
Figure 12:
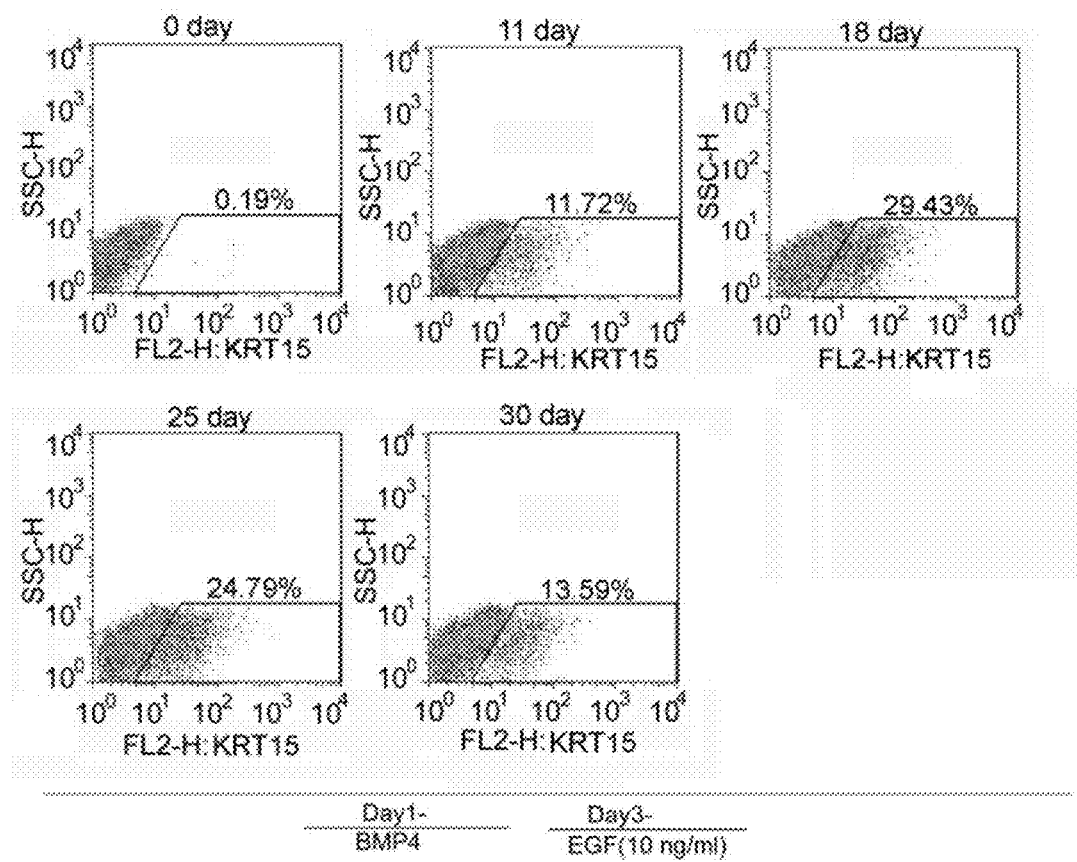
FIG. 12. Flow cytometric analysis of positive cells for KRT15 during keratinocyte differentiation from hiPSCs. Flow cytometric analysis was performed using antibody specific for KRT15 and KRT15+ cell percentage was monitored at 0, 11, 18, 25 and 30 days respectively.

CD200 (also known as OX2) and alpha 6 integrin (ITGA6, also known as CD49f) are known surface markers for hEpSCs within hair follicles[12]. To generate folliculogenic hEpSCs from hiPSCs, we firstly followed the prior keratinocyte differentiation protocols[18-21]. We monitored the temporal expression of CD200 and ITGA6 in differentiating hiPSCs using flow cytometric analysis and found that only few cells expressing both CD200 and ITGA6 emerged after 11, 18 of 25 days of differentiation using these protocols (FIGS. 6 and 7). To generate a sufficient number of hEpSCs from hiPSCs, we tried different methods and found that timing of EGF in the culture medium was critical (see FIGS. 6, 7, 8 and 9). We established a new sequential differentiation protocol that used retinoic acid (RA) to induce hiPSC to form ectodermal like cells (stage 1, FIG. 10A), which were then differentiated to form hEpSCs in the presence of BMP4 and EGF (stage 2, FIG. 10A), followed by the final expansion of the mature keratinocyte lineages in the presence of EGF alone (stage 3, FIG. 10A). The morphology of the expected cell types at stage 2 and 3 was shown in FIG. 10B. Using this stage defined differentiation protocol, we recapitulated the dynamic differentiation process from pluripotent stem cells to EpSCs and then to mature keratinocytes; thus capturing the EpSCs, a transient multipotent stem cell population in vitro. Using the sequential differentiation protocol, the $CD200^+/ITGA6^+$ cells emerged around day 11 after differentiation (FIG. 9), and reached a maximum level of 26.8±3.0% around day 18 after differentiation (FIGS. 11C, 11F and FIG. 9). The appearance of the keratin (KRT15)-positive ($KRT15^+$) cells, which reached 29.4±4.0% by day 18 (FIGS. 10D, 10G and FIG. 12), closely paralleled the appearance of the $CD200^+/ITGA6^+$ population. We further analyzed the percentage of $CD200^+/KRT15^+$, $CD200^+$/keratin 14 (KRT14)-positive ($KRT14^+$), $KRT15^+/ITGA6^+$, $KRT14^+/ITGA6^+$ and $KRT15^+/KRT14^+$ cell populations at day 18.

Figure 13:
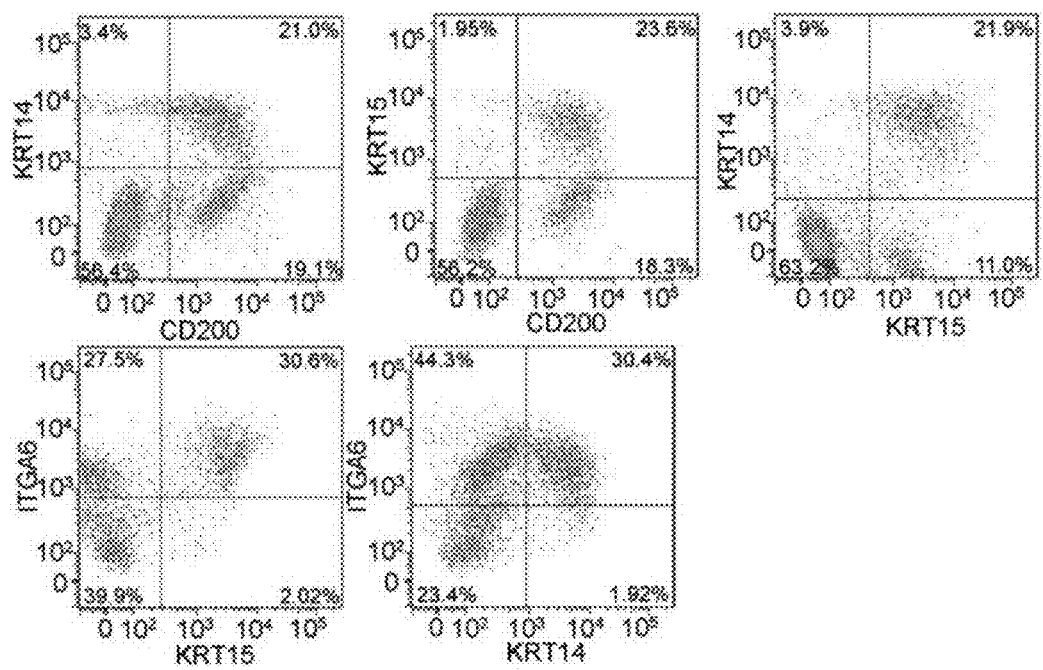
FIG. 13. Flow cytometric analysis of staged expression of analyzed the percentage of CD200+/KRT15+, CD200+/KRT14+, ITGA6+/KRT15+, ITGA6+/KRT14+ and KRT14+/KRT15+ cell populations at day 18.
Figure 14:
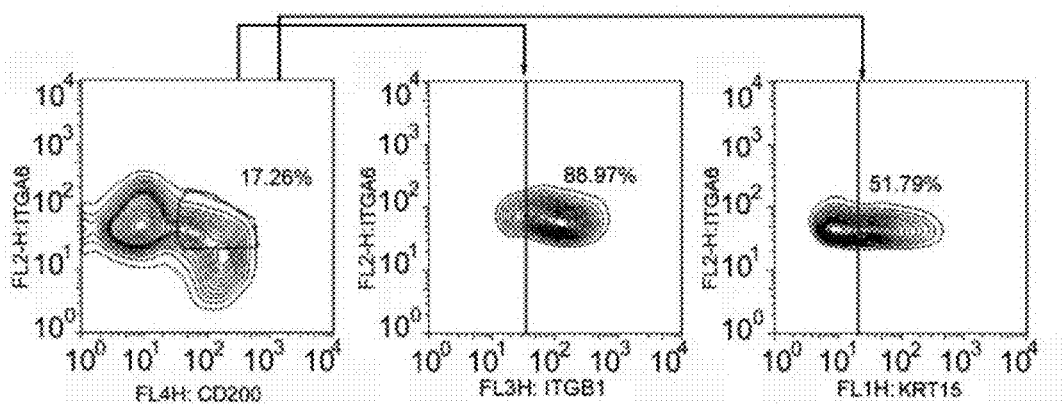
FIG. 14. Flow cytometric analysis of ITGB1+ or KRT5+ cell percentage in CD200+/ITGA6+ cells. CD200+/ITGA6+ cell population was gated out. Almost all the cells expressed ITGB1 and only about 50% cells expressed KRT15.
Figure 15:
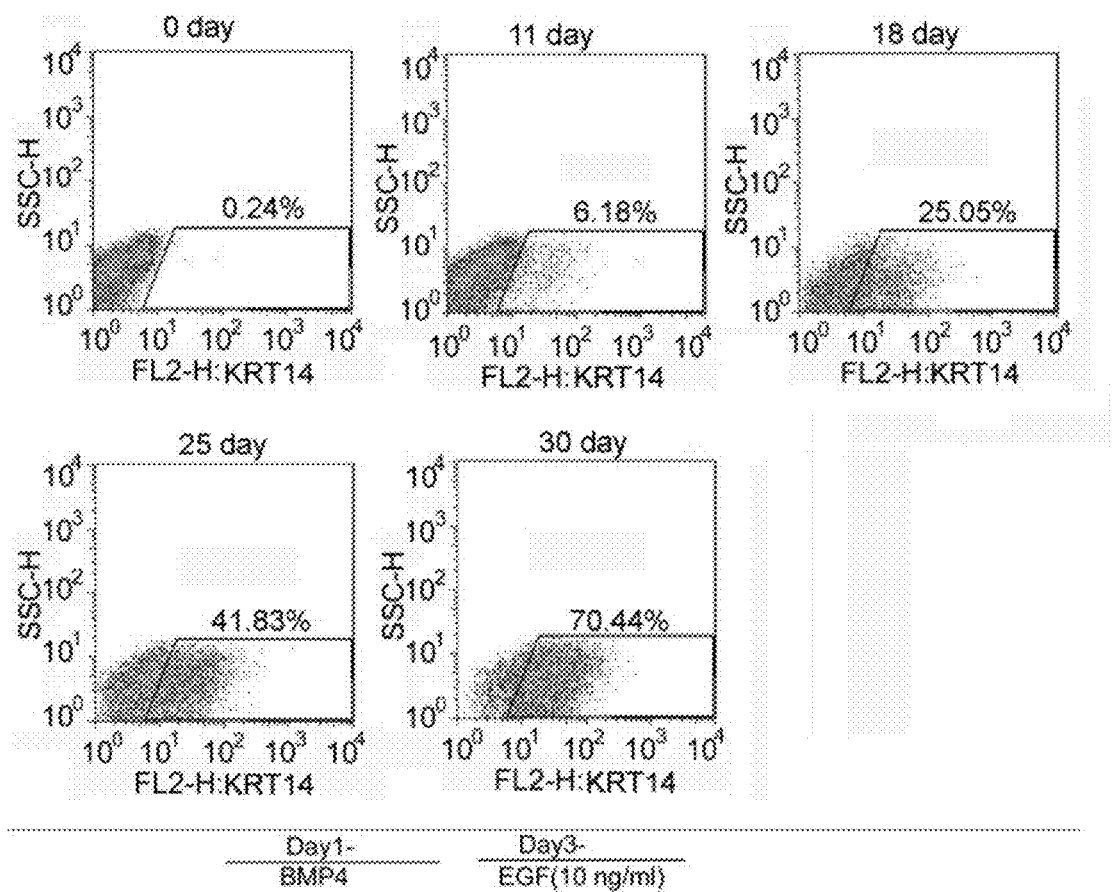
FIG. 15. Flow cytometric analysis of positive cells for KRT14 during keratinocyte differentiation from hiPSCs. Flow cytometric analysis was performed using antibody against KRT14 and KRT14+ cell percentage was monitored at 0, 11, 18, 25 and 30 days respectively.
Figure 16:
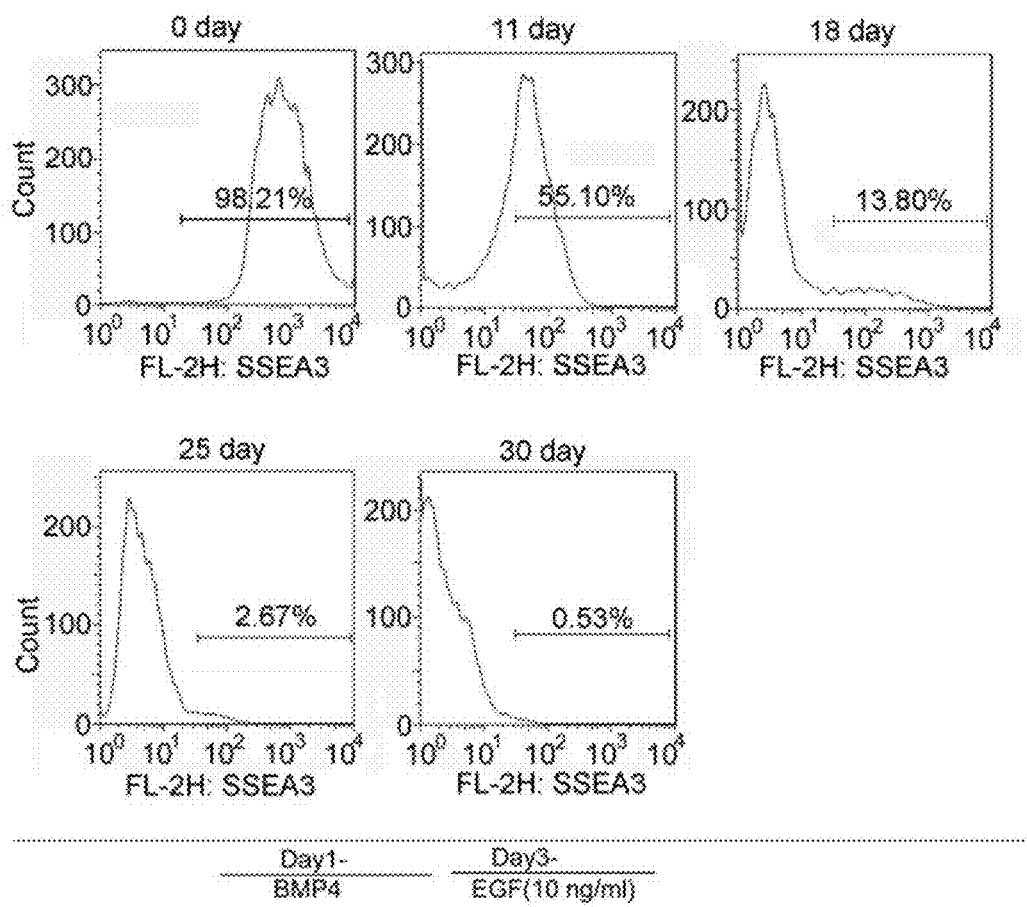
FIG. 16. Flow cytometric analysis of positive cells for SSEA3 during keratinocyte differentiation from iPSCs. Flow cytometric analysis was performed using antibody specific for SSEA3 and SSEA3+ cell percentage was monitored at 0, 11, 18, 25 and 30 days respectively.
Figure 17:
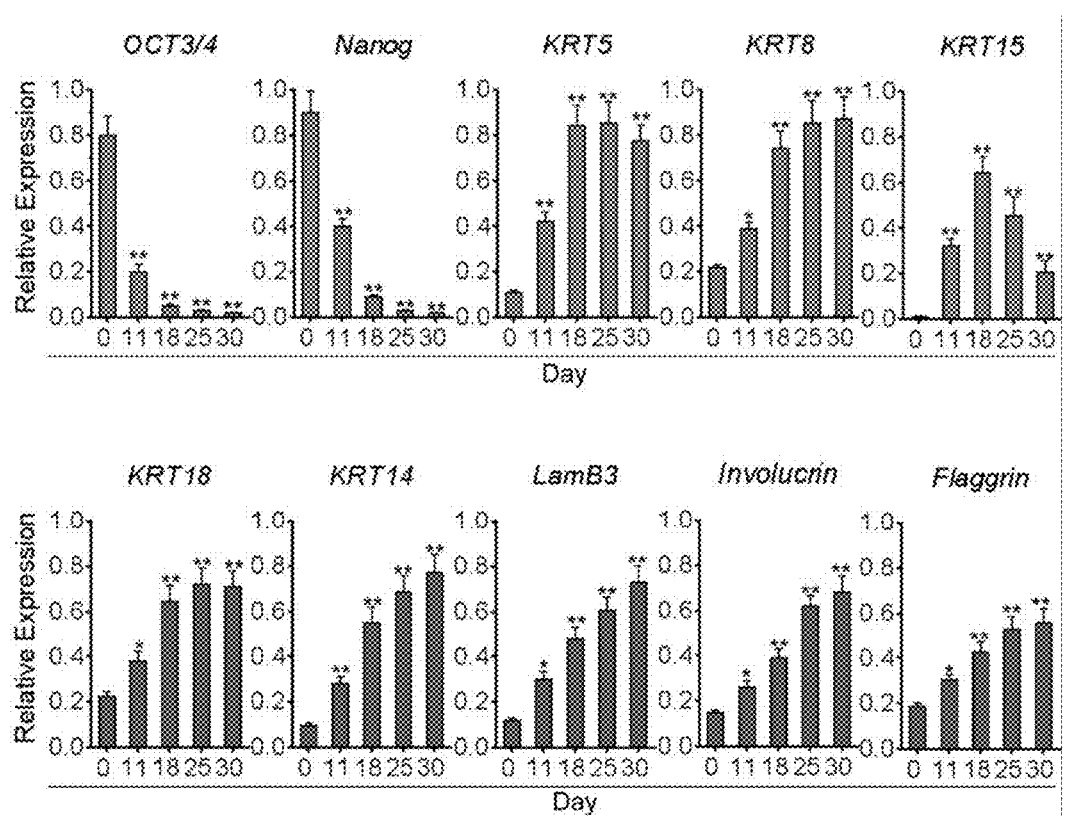
FIG. 17. qPCR analysis of OCT3/4, NANOG, KRT5, KRTB, KRT14, KRT15, LamB3, Involucrin and Faggrin in hiPSC-derived cells at different stages of differentiation. Data shown are mean±SO of cell percentage from three independent experiments. * indicates p<0.05 and ** indicates p<0.01. The expression of OCT3/4 and Nanog decreased significantly at day 11, 18, 25 and 30 compared with the expresson at day 0. Conversely, the expression of KRT5, KRTB, KRT15, KRT1B, KRT14, LamB3, Involucrin and Flaggrin increased significantly at day 11, 18, 25 and 30 compared with the expression at day 0. The expression of KRT5 at day 18, 25 and 30 was not significantly different although its expression seemed decrease at day 30. The expression of KRT15 decreased significantly at day 30 compared with the expression at day 18(P<0.01).

The results demonstrated that these populations did not overlap completely (FIG. 13). We analyzed the percentage of $KRT15^+$ and $ITGB1^+$ expression among the $CD200^+/ITGA6^+$ cells. Similar to the prior study[11], we found that only about 50% of $CD200.sup.^+/ITGA6^+$ cells expressed KRT15 (FIG. 17). As expected from our prior experience with hair follicle-derived EpSCs, the $CD200^+/ITGA6^+$ population was not stable in culture and their number decreased significantly after day 25 (FIG. 10F and FIG. 9); whereas, $KRT14^+$ mature keratinocytes increased steadily over time (FIGS. 10E, 10H and FIG. 15), indicating differentiation of hiPSC-derived $CD200^+/ITGA6^+$ cells to more mature keratinocytes. Correspondingly, flow cytometric analysis showed that the pluripotent stem cell ($SSEA3^+$) population decreased progressively during differentiation (FIG. 16).

We also analyzed the temporal gene expression profile of the differentiating cultures and the results demonstrated a step-wise progression from embryonic immature cells ($OCT3/4^+$ and $NANOG^+$) to epithelial lineages, characterized by keratin 5 (KRT5) and keratin 8 (KRT8) expression, around 11 days after induction (FIG. 10I and FIG. 17). The expression of keratinocyte-specific genes in the differentiating hiPSC-derived culture increased over time, with concomitant decrease in OCT3/4 and NANOG expression (FIG. 10I and FIG. 17). Consistent with flow cytometric analysis results, the expression of KRT15, began around day 11, peaked around day 18, and then decreased significantly by day 30 (FIG. 10I and FIG. 17).

CD200 has been recently reported to be expressed in hiPSCs and hESCs[22]. Our data confirmed the expression of CD200 in iPSCs, we found its expression later retained in a subpopulation of ITGA6$^+$ cells as hiPSCs differentiated. No other pluripotent stem cell markers, such as OCT3/4, NANOG and REX1, were detected in cells isolated at day 18 from the CD200$^+$/ITGA6$^+$ population (FIG. 18), confirming that the hiPSC-derived CD200$^+$/ITGA6$^+$ cells contain few undifferentiated hiPSCs.

Figure 18:
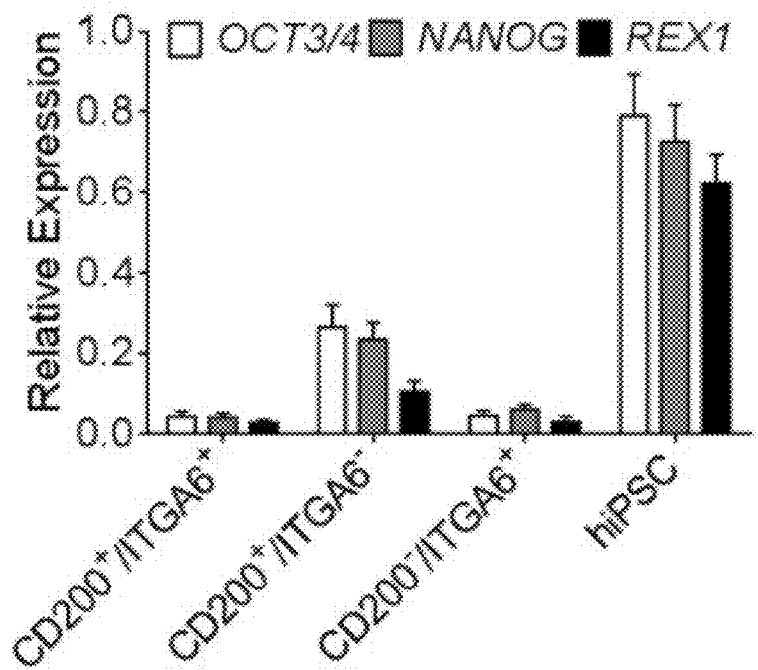
FIG. 18. qPCR analysis of pluripotent stem cell markers in the hiPSC-derived CD200+/ITGA6+ cells, hiPSC-derived CD200+/ITGA6− cells, hiPSC-derived CD200−/ITGA6+ cells and hiPSCs. The pluripotent stem cell markers include OCT3/4, NANOG and REX1.
Figure 19:
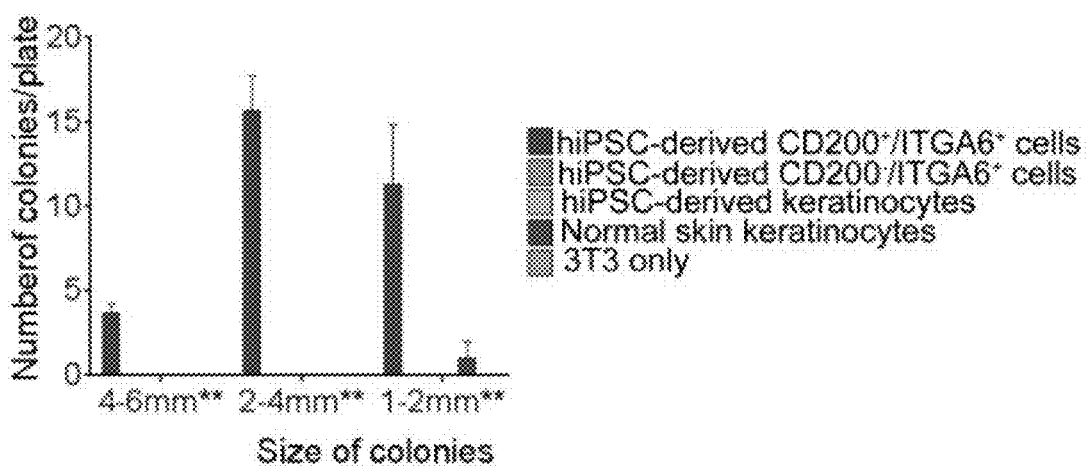
FIG. 19. Quantification of size and number of colonies from hiPSC-derived CD200+/ITGA6+ cells, hiPSC-derived CD200−/ITGA6+ cells, hiPSC-derived mature keratinocytes and Normal skin-derived mature keratinocytes(normal skin keratinocytes). The graph summarizes results from one of three experiments, which all yielded similar results. ** denotes a significant difference (P<0.01) colony numbers between hiPSC-derived CD200+/ITGA6+ cells and the other cell populations. 3T3 feeder cells used as a negative control.

EpSCs are known to have high colony forming efficiency[9]. We compared the colony forming efficiency of unfractionated cells hiPSC-derived CD200$^+$/ITGA6$^+$ cells, hiPSC-derived CD200$^-$/ITGA6$^+$ cells, hiPSC-derived CD200$^+$/ITGA6$^-$ cells at day 18 after differentiation; hiPSC-derived mature keratinocytes and normal skin-derived mature keratinocytes isolated as previously described[9]. We found that hiPSC-derived CD200$^+$/ITGA6$^+$ cells had the highest colony forming efficiency among all the epithelial cells, as demonstrated by the higher number and larger size of colonies, compared to the other epithelial cell populations, after 3 weeks in culture (FIG. 11A and FIG. 19). Nevertheless, the unfractionated cells at day 18 formed the most colonies among all the cells tested and hiPSC-derived CD200$^+$/ITGA6$^-$ cells formed a similar number of colonies as hiPSC-derived CD200$^+$/ITGA6$^+$ cells. However, since there were non-epithelial and undifferentiated cells in CD200$^+$/ITGA6$^-$ populations, the colonies formed by these cells had different morphology as CD200$^+$/ITGA6$^+$ cells (data not shown). Indeed, hiPSC-derived CD200$^+$/ITGA6$^-$ cells expressed stem cell markers, including OCT3/4 and NANOG (FIG. 18).

Figure 20:
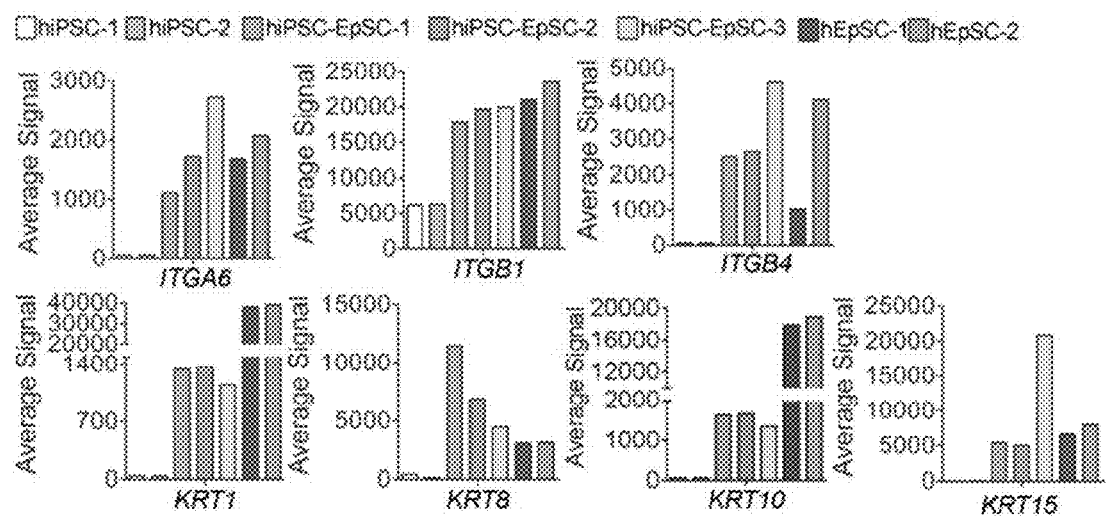
FIG. 20. Microarray analysis of the expression of KRT1, KRTB, KRT15, ITGA6, 1TGB1 and ITGB4 in hiPSCs, hiPSC-derived EpSCs and hEpSCs from hair follicles. KRT1, KRTB, KRT15, ITGA6, ITGB1 and ITGB4 were selected and the expression data were shown from raw data of microarray.

Transcriptional analysis of CD200$^+$/ITGA6$^+$ cells by qPCR confirmed the activation of EpSC-specific network genes such as LGR5[23], LGR6[24], FZD2, TCF4, DKK3, CTNNB1, LEF1 and LHX2[25] in CD200$^+$/ITGA6$^+$ cells (FIG. 11B). Immunocytochemical stains confirmed the expression of KRT1, KRT10, KRT15 and ITGB1 expression in the day 18 cell culture after differentiation (FIGS. 11C-11F); short-term culture of CD200$^+$/ITGA6$^+$ EpSCs isolated from human hair follicles was used as a control. To further compare the gene expression signature of hiPSC-derived EpSCs to EpSCs in human hair follicles, we analyzed global gene expression patterns of CD200$^+$/ITGA6$^+$ cells isolated from human fetal hair follicles, CD200$^+$/ITGA6$^+$ cells derived from hiPSCs and the parental hiPSCs. The results showed that hiPSC-derived CD200$^+$/ITGA6$^+$ cells clustered with CD200$^+$/ITGA6$^+$ cells isolated from fetal hair follicles, and were distinctively different from the parental hiPSCs as illustrated by unsupervised hierarchical clustering analysis (FIGS. 11G and 11H). Notably, there was considerable overlap of genes between hiPSC-derived and hair follicle-derived CD200$^+$/ITGA6$^+$ cells (FIG. 2I); with many representative genes of epithelial lineages, such as KRT1, KRT8, KRT10, KRT15, ITGB1 and ITGA6 being highly enriched in the CD200$^+$/ITGA6$^+$ population compared to the parental hiPSC cells and their expression levels were similar to EpSCs isolated from human hair follicles (FIG. 20). Conversely, expression of the markers of ESCs, such as SOX2 and NANOG, decreased in the hiPSC-derived CD200$^+$/ITGA6$^+$ cell population (FIG. 11J). These findings indicate that the hiPSC-derived CD200$^+$/ITGA6$^+$ cells share similar molecular signatures with human EpSCs isolated from hair follicles.

EpSCs located in the bulge of the hair follicle have been documented to play a crucial role in hair follicle growth and cycling[9, 26]. Although CD200$^+$ and ITGA6$^+$ are surface markers for human EpSCs[12], it is unknown whether human CD200$^+$/ITGA6$^+$ cells isolated from adult scalp can form hair follicles in skin reconstitution assays. To determine if hiPSC-derived EpSCs are multipotent and capable of generating all of the epithelial lineages within the skin, we first performed a patch assay[27, 28] for skin reconstitution using day 18 hiPSC-derived CD200$^+$/ITGA6$^+$ cells which were enriched by Fluorescence-activated cell sorting (FACS) or magnetic bead selection. We found that the magnetic bead approach enabled isolation of large numbers of cells required for in vivo studies with minimal damage to the cells[29]. To minimize contamination of undifferentiated pluripotent stem cells and potential tumorigenesis[30, 31], we depleted potential remaining undifferentiated hiPSCs in the CD200$^+$/ITGA6$^+$ population using magnetic beads conjugated with antibody against the hiPSC membrane marker SSEA3. Neonatal foreskin-derived keratinocytes were used as a positive control, whereas hiPSC-derived CD200$^-$/ITGA6$^+$ at day 18 or mature keratinocytes isolated from hair bearing normal human skin were used as negative controls. The hiPSC-derived CD200$^+$/ITGA6$^+$ or control cells were combined with neonatal mouse dermal cells and injected subcutaneously into the back skin of immune-deficient nude mice. Two and half weeks later the skins of the mice were then excised and examined under a dissecting microscope. Hair follicle-like structures were seen from the underside of the skin (FIG. 21A). Histological analysis revealed that the injected epithelial cells aggregated to form small cystic spheres in the host subcutis. The cysts consisted of both basal keratinocytes and stratified epidermis. Hair follicles growing outward from the cyst were evident (FIG. 21B). This phenomenon was similar to what was observed previously in skin reconstitution assays using mouse EpSCs and neonatal dermal cells[9, 27, 28]. The neonatal foreskin-derived keratinocytes also formed hair follicles while the negative control cells (hiPSC, CD200$^-$/ITGA6$^+$ cells and normal skin-derived keratinocytes) did not form any hair follicles under the same condition (data not shown). Compared with hiPSC-derived mature keratinocytes, neonatal foreskin-derived keratinocytes contains CD200$^+$/ITGA6$^+$ and KRT15$^+$ cell populations. qPCR results further confirmed that neonatal foreskin-derived keratinocytes mildly expressed epithelial stem cell markers. (FIGS. 22A and 22B). The human origin of the epithelial cells in the new hair follicle structures and interfollicular epidermis was confirmed by DNA in situ hybridization with a human-specific Alu-repeat sequence probe (FIG. 21C). Double DNA in situ hybridization with human and mouse pan-centromeric probes further confirmed that the hair follicle epithelium and interfollicular epidermis were of human origin and the surrounding mesenchymal components were composed of mouse cells (FIGS. 21D and 21E). In addition, when we used hiPSCs-derived mature keratinocytes which contains few CD200$^+$/ITGA6$^+$ and KRT15$^+$ cells (FIG. 22A) in the patch assays, we only observed stratified epidermis but no hair follicles were present (data not shown). To further confirm the folliculogenic capacity of hiPSCs-derived EpSCs, we performed a chamber-based skin reconstitution assay[32] using hiPSC-derived EpSCs and neonatal mouse dermal cells. hiPSC-derived EpSCs were mixed with C57BL/6 neonatal dermal fibroblasts in a chamber and transplanted onto mouse back skin. 3 weeks later hair follicle-like structures were observed in the grafts (FIG. 21F). Histological examination showed human-like hair follicles in the grafts and hair shafts which are distinctively different from mouse hair shafts were present in the hair follicles (FIG. 21G). Human skin-like multilayered epidermis was also formed within the grafts (FIG. 21H). The newly formed epidermis was impermeable to toluidine blue dye indicating a functional skin barrier (FIG. 23). The human origin of the epithelial cells in the hair follicles and interfollicular epidermis was confirmed by DNA in situ hybridization with a human-specific Alu-repeat sequence probe (FIGS. 21I and 21J).

Next, we performed immunostaining to characterize the hair follicles and epidermis originated from iPSC-EpSCs. We found that KRT15 was expressed in the bulge region of the chimeric hair follicles (FIG. 24A), similar to hair follicles formed by neonatal foreskin-derived keratinocytes. Other keratinocyte markers, such as KRT14, were detected in the outer root sheath of the chimeric hair follicles (FIG. 24B). H&E staining showed that the innermost regions of the chimeric hair follicle structures resembled the hair cortex and the medulla of mature human hair follicles (FIGS. 24C, 24D and 24E). The formation of such structures were further confirmed by immunohistochemical staining for AE13, a marker for hair follicle cortex, and AE15, a marker for inner root sheath and medulla, in a pattern that is similar to normal human hair follicles (FIGS. 24C, 24D and FIG. 25). We also found K75 expressed specifically in the companion layer of the chimeric hair follicle (FIG. 24Ee and FIG. 26). The hiPSC-derived CD200$^+$/ITGA6$^+$ cells not only reconstituted the epithelial components of the hair follicle but also the interfollicular epidermis. The multilayered interfollicular epidermis expressed KRT10 and involucrin (FIGS. 24F and 24G). Our findings indicate that hiPSC-derived CD200$^+$/ITGA6$^+$ cells are capable of generating functional epidermis and responding to inductive dermal signals to generate the epithelial component of hair follicles.

To further define the differentiation capacity of hiPSC-derived CD200$^+$/ITGA6$^+$ cells, we cultured these cells under sebocyte differentiation conditions as previous described[33]. Three weeks after differentiation, some of the cells acquired abundant cytoplasm with oil droplets and the oil droplets were positive for oil red staining (FIG. 27A). The sebocyte-like cells also expressed sebocyte markers, such as keratin 7 (KRT 7), peroxisome proliferator-activated receptor alpha (PPAR-α or PPARA) and lipoprotein lipase (LPL), as shown by qPCR (FIG. 27B). These results indicate that CD200$^+$/ITGA6$^+$ are capable of sebocyte differentiation. In order to generate mature keratinocytes from hiPSC-derived CD200$^+$/ITGA6$^+$ cells, the hiPSC-derived CD200$^+$/ITGA6$^+$ cells were cultured for an additional 25 days in the presence of EGF until the KRT14$^+$ keratinocytes population reached 98.8% purity (FIG. 28) as shown by Flow cytometric analysis, whereas CD200$^+$/ITGA6$^-$ cells cultured under the same conditions resulted in only 18.0% KRT14$^+$ keratinocytes.

Figure 29:
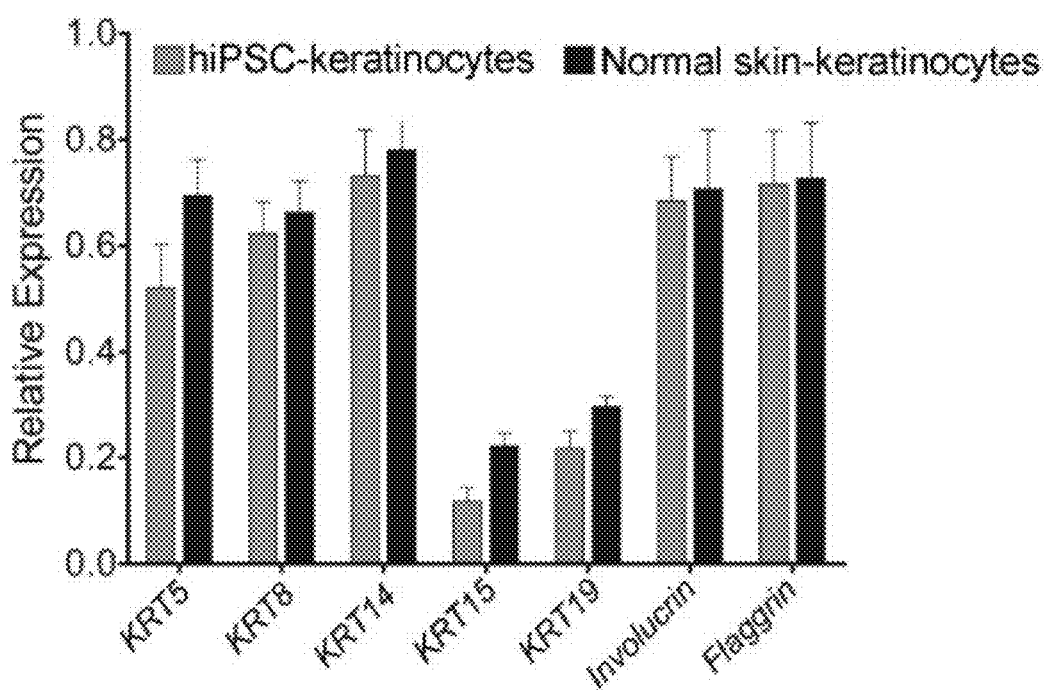
FIG. 29. qPCR analysis of keratinocyte marker. Keratinocyte markers, including KRT5, KRTB, KRT14, KRT15, KRT1, Involucrin and Flaggrin, were analyzed by qPCR in hiPSC-derived mature keratinocytes (hiPSCkeratinocytes) and normal skin-derived keratinocytes(Normal skin-keratinocytes).
Figure 30:
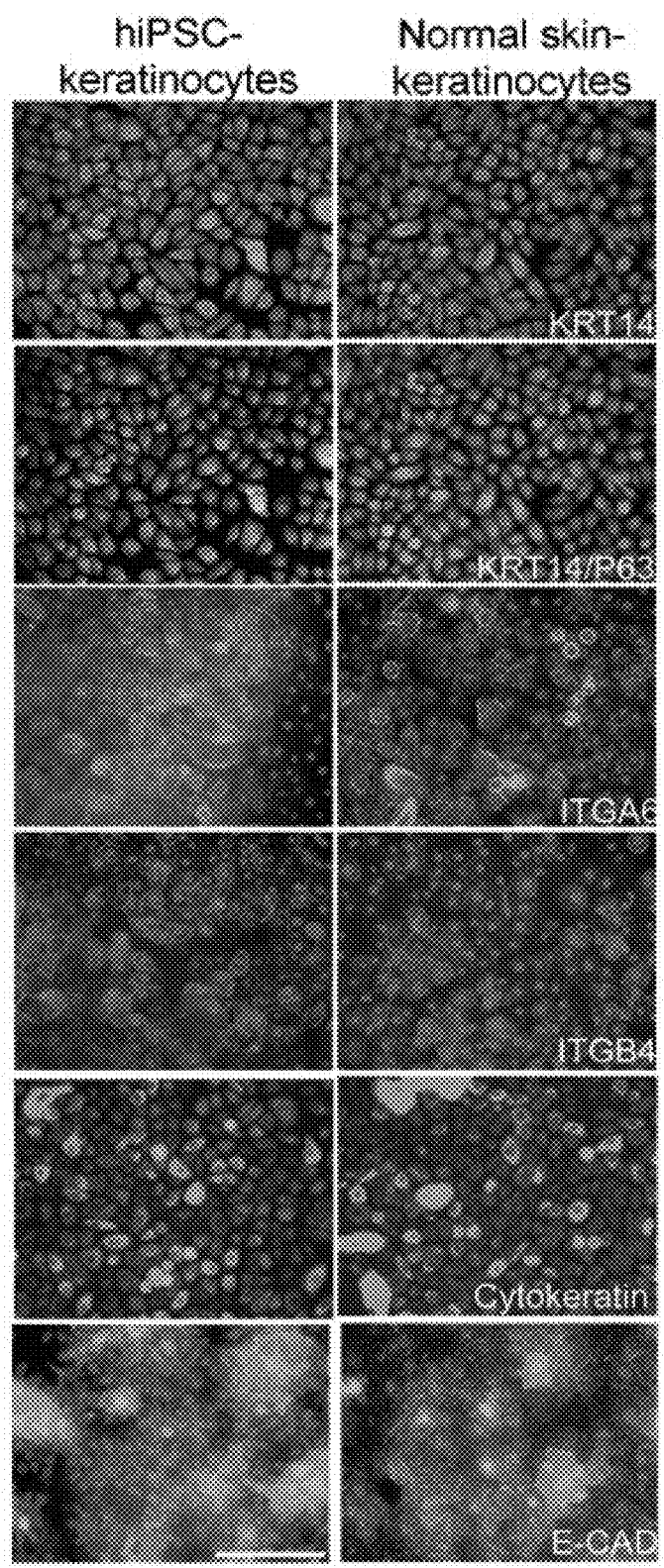
FIG. 30. Immunostaining analysis of keratinocyte markers, including KRT14, P63, ITGA6, Pan-cytokeratin, ITGB4 and E-CAD (E-cadherin) in hiPSC-derived mature keratinocytes (hiPSC-keratinocyte) and normal skin-derived keratinocytes (Normal skin-keratinocytes. Scale bar, 20 µm.
Figure 31:
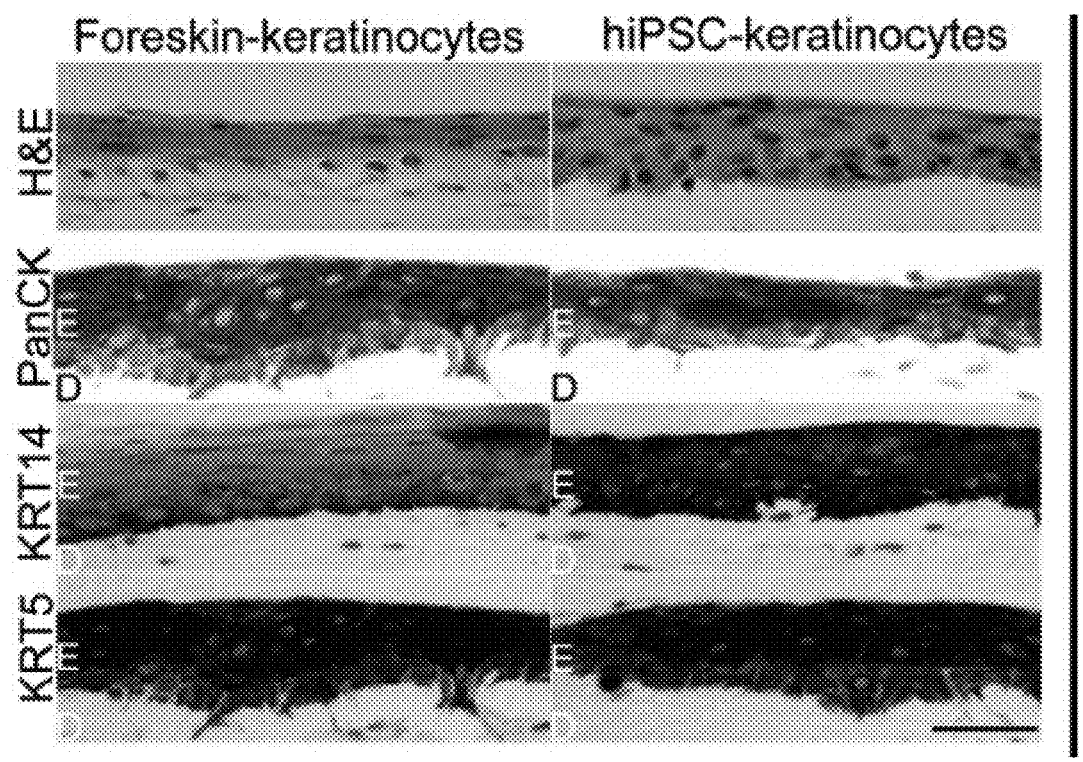
FIG. 31. 3D skin equivalents using hiPSC-derived mature keratinocytes. H&E staining of 3D skin equivalents. The multilayered epidermis expressed Pan-cytokeratin, KRT5 and KRT14 in 3D skin equivalents using neonatal foreskin-derived keratinocytes (Foresknkeratinocytes) or hiPSC-derived mature keratinocytes (hiPSC-keratinocytes). Scale bar, 30 um.

Transcriptional analysis by qPCR showed that KRT14$^+$ keratinocytes derived from hiPSC expressed a panel of epidermal genes similar to those of normal human keratinocytes (FIG. 29). Immunostaining analysis showed that most cells expressed mature squamous cell markers, such as keratin proteins (KRT14), integrins (ITGA6 and ITGB4) and the epithelial marker E-cadherin (also known as CDH1) (FIG. 30). We next generated 3D skin equivalents using keratinocytes from neonatal foreskin and mature keratinocytes from hiPSC-derived CD200$^+$/ITGA6$^+$ cells. The 3D skin equivalents exhibited a multilayered epidermis, expressing squamous differentiation markers, such as KRT14 and KRT5, and Pan-cytokeratin (PanCK) (FIG. 31), in a pattern similar to skin equivalents formed by neonatal foreskin-derived keratinocytes (FIG. 31). These data support that hiPSC-derived CD200$^+$/ITGA6$^+$ cells are multipotent.

However, surprisingly, we were not able to identify human sebaceous glands derived from the hiPSC-derived CD200$^+$/ITGA6$^+$ cells or neonatal foreskin derived keratinocytes in the skin reconstitution assays. It is well known that mouse EpSCs (CD34$^+$/ITGA6$^+$ or KRT15$^{high}$/ITGA6$^+$) are capable of regenerating both follicular epithelium and sebaceous units in the skin reconstitute assays[9, 34]. These results suggest that hiPSC-derived CD200$^+$/ITGA6$^+$ cells, although folliculogenic and sharing molecular signatures similar to those of human EpSCs, are likely more restricted in their lineage potential compared with EpSCs or they may require additional signals for sebocyte differentiation in vivo.

Previous studies demonstrated that mouse iPSC-derived multipotent keratinocyte induced by BMP4 to reconstitute normal skin and its appendages in an in vivo assay[35]. Veraitch O et al used a similar protocol and found that the hiPSCs-derived ectodermal precursor cells emerged at day 11 contribute to human hair follicle morphogenesis[36]. However, it was unclear from the study which cell population in the ectodermal cells contributed to folliculogenesis and low frequency of human derived cells in the hair follicles observed in the study implied that these cells contribute to hair follicle morphogenesis via direct repopulation and non-cell autonomous activities. We observed few CD200$^+$/ITGA6$^+$ cells at day 11 when we tested a similar protocol without using EGF; and over 30% of the cells retained expression of SSEA3 (FIG. 7) which are potentially tumorigenic.

In conclusion, we discovered a novel hiPSC differentiation method that efficiently differentiates hiPSCs to EpSCs, and these CD200$^+$/ITGA6$^+$ cells have similar molecular characteristics of hEpSCs. hiPSC-derived CD200$^+$/ITGA6$^+$ cells isolated by magnetic beads provide a simple approach for generating highly enriched populations of folliculogenic human cells which can reconstitute the hair follicle epithelial components and interfollicular epidermis in vivo. Our study establishes a means for obtaining a scalable source of CD200$^+$/ITGA6$^+$ cells, which is a major step toward developing cell-based treatments for hair loss and other skin disorders. Production of Nevertheless, access to cells with cardinal features of hEpSCs opens new possibilities for studying regenerative therapies for hair loss, wound healing and aging skin.

REFERENCES

1. Lee, G. et al. Modelling pathogenesis and treatment of familial dysautonomia using patient-specific iPSCs. Nature 461, 402-406 (2009).
2. Raya, A. et al. Disease-corrected haematopoietic progenitors from Fanconi anaemia induced pluripotent stem cells. Nature 460, 53-59 (2009).
3. Ebert, A. D. et al. Induced pluripotent stem cells from a spinal muscular atrophy patient. Nature 457, 277-280 (2009).
4. Dimos, J. T. et al. Induced pluripotent stem cells generated from patients with ALS can be differentiated into motor neurons. Science 321, 1218-1221 (2008).
5. Hanna, J. et al. Treatment of sickle cell anemia mouse model with iPS cells generated from autologous skin. Science 318, 1920-1923 (2007).
6. Soldner, F. et al. Parkinson's disease patient-derived induced pluripotent stem cells free of viral reprogramming factors. Cell 136, 964-977 (2009).
7. Ito, M. et al. Stem cells in the hair follicle bulge contribute to wound repair but not to homeostasis of the epidermis. Nat Med 11, 1351-1354 (2005).

8. Ito, M. et al. Wnt-dependent de novo hair follicle regeneration in adult mouse skin after wounding. Nature 447, 316-320 (2007).
9. Morris, R. J. et al. Capturing and profiling adult hair follicle stem cells. Nat Biotechnol 22, 411-417 (2004).
10. Liu, Y., Lyle, S., Yang, Z. & Cotsarelis, G. Keratin 15 promoter targets putative epithelial stem cells in the hair follicle bulge. J Invest Dermatol 121, 963-968 (2003).
11. Garza, L. A. et al. Bald scalp in men with androgenetic alopecia retains hair follicle stem cells but lacks CD200-rich and CD34-positive hair follicle progenitor cells. J Clin Invest 121, 613-622 (2011).
12. Ohyama, M. et al. Characterization and isolation of stem cell-enriched human hair follicle bulge cells. J Clin Invest 116, 249-260 (2006).
13. Cotsarelis, G. & Millar, S. E. Towards a molecular understanding of hair loss and its treatment. Trends Mol Med 7, 293-301 (2001).
14. Takahashi, K. & Yamanaka, S. Induction of pluripotent stem cells from mouse embryonic and adult fibroblast cultures by defined factors. Cell 126, 663-676 (2006).
15. Takahashi, K. et al. Induction of pluripotent stem cells from adult human fibroblasts by defined factors. Cell 131, 861-872 (2007).
16. Nakagawa, M. et al. Generation of induced pluripotent stem cells without Myc from mouse and human fibroblasts. Nat Biotechnol 26, 101-106 (2008).
17. Park, I. H. et al. Reprogramming of human somatic cells to pluripotency with defined factors. Nature 451, 141-146 (2008).
18. Metallo, C. M., Ji, L., de Pablo, J. J. & Palecek, S. P. Retinoic acid and bone morphogenetic protein signaling synergize to efficiently direct epithelial differentiation of human embryonic stem cells. Stem Cells 26, 372-380 (2008).
19. Guenou, H. et al. Human embryonic stem-cell derivatives for full reconstruction of the pluristratified epidermis: a preclinical study. Lancet 374, 1745-1753 (2009).
20. Itoh, M., Kiuru, M., Cairo, M. S. & Christiano, A. M. Generation of keratinocytes from normal and recessive dystrophic epidermolysis bullosa-induced pluripotent stem cells. Proc Natl Acad Sci USA 108, 8797-8802 (2011).
21. Nissan, X. et al. Functional melanocytes derived from human pluripotent stem cells engraft into pluristratified epidermis. Proc Natl Acad Sci USA 108, 14861-14866 (2011).
22. Tang, C. et al. An antibody against SSEA-5 glycan on human pluripotent stem cells enables removal of teratoma-forming cells. Nat Biotechnol 29, 829-834 (2011).
23. Jaks, V. et al. Lgr5 marks cycling, yet long-lived, hair follicle stem cells. Nat Genet 40, 1291-1299 (2008).
24. Snippert, H. J. et al. Lgr6 marks stem cells in the hair follicle that generate all cell lineages of the skin. Science 327, 1385-1389 (2010).
25. Janich, P. et al. The circadian molecular clock creates epidermal stem cell heterogeneity. Nature 480, 209-214 (2011).
26. Cotsarelis, G., Sun, T. T. & Lavker, R. M. Label-retaining cells reside in the bulge area of pilosebaceous unit: implications for follicular stem cells, hair cycle, and skin carcinogenesis. Cell 61, 1329-1337 (1990).
27. Zheng, Y. et al. Organogenesis from dissociated cells: generation of mature cycling hair follicles from skin-derived cells. J Invest Dermatol 124, 867-876 (2005).
28. Zheng, Y. et al. Mature hair follicles generated from dissociated cells: a universal mechanism of folliculoneogenesis. Dev Dyn 239, 2619-2626 (2010).
29. Dubois, N. C. et al. SIRPA is a specific cell-surface marker for isolating cardiomyocytes derived from human pluripotent stem cells. Nat Biotechnol 29, 1011-1018 (2011).
30. Ghosh, Z. et al. Dissecting the oncogenic and tumorigenic potential of differentiated human induced pluripotent stem cells and human embryonic stem cells. Cancer Res 71, 5030-5039 (2011).
31. Tong, M. et al. Mice generated from tetraploid complementation competent iPS cells show similar developmental features as those from ES cells but are prone to tumorigenesis. Cell Res 21, 1634-1637 (2011).
32. Ehama, R. et al. Hair follicle regeneration using grafted rodent and human cells. J Invest Dermatol 127, 2106-2115 (2007).
33. Roh, C. et al. Multi-potentiality of a new immortalized epithelial stem cell line derived from human hair follicles. In Vitro Cell Dev Biol Anim 44, 236-244 (2008).
34. Trempus, C. S. et al. Enrichment for living murine keratinocytes from the hair follicle bulge with the cell surface marker CD34. J Invest Dermatol 120, 501-511 (2003).
35. Bilousova, G., Chen, J. & Roop, D. R. Differentiation of mouse induced pluripotent stem cells into a multipotent keratinocyte lineage. J Invest Dermatol 131, 857-864 (2011).
36. Veraitch, O. et al. Human Induced Pluripotent Stem Cell-Derived Ectodermal Precursor Cells Contribute to Hair Follicle Morphogenesis In Vivo. J Invest Dermatol (2013).
37. Yang, R. et al. Generation of melanocytes from induced pluripotent stem cells. J Invest Dermatol 131, 2458-2466 (2011).
38. Kishimoto, J. et al. Selective activation of the versican promoter by epithelial-mesenchymal interactions during hair follicle development. Proc Natl Acad Sci USA 96, 7336-7341 (1999).
39. Du, P., Kibbe, W. A. & Lin, S. M. lumi: a pipeline for processing Illumina microarray. Bioinformatics 24, 1547-1548 (2008).
40. Smyth, G. K. Linear models and empirical bayes methods for assessing differential expression in microarray experiments. Stat Appl Genet Mol Biol 3, Article3 (2004).
41. Smyth, G. K. in Bioinformatics and Computational Biology Solutions using R and Bioconductor. (eds. R. Gentleman, S. D. V. Carey, R. Irizarry & W. Huber) (Springer, New York; 2005).
42. Benjamini, Y. & Hochberg, Y. Controlling the false discovery rate: a practical and powerful approach to multiple testing. Journal of the Royal Statistical Society. Series B 57, 289-300 (1995).

While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. A method for differentiating human induced pluripotent stem cells (hiPSC) into hair follicles and interfollicular epidermis comprising the steps of:
(a) transducing isolated human dermal fibroblasts with nucleic acids encoding OCT3/4, SOX2 and KLF4 to obtain hiPSCs, (b) culturing the hiPSCs of step (a) in a fresh medium comprising BMP4,
(c) culturing the cells of step (b) in a fresh medium comprising retinoic acid (RA),
(d) culturing the cells of step (c) in a fresh medium comprising RA, BMP4 and EGF,
(e) culturing the cells of step (d) in a fresh medium comprising BMP4 and EGF to obtain human epithelial stem cells (hEpSCs) which express CD200, ITGA6, and KRT15; and
(f) culturing the hEpSCs of step (e) under conditions to obtain hair follicles and interfollicular epidermis.

2. The method of claim 1, wherein said hiPSCs are differentiated over a 25 day period and the BMP4 in step (b) is present at days 0-1, the RA in step (c) is present at days 1 to 11, the RA, BMP4 and EGF in step (d) are present from days 3-11 and the BMP4 and EGF in step (e) are present from days 11 to 25, and said method further comprises expanding said hEpSCs obtained in step (e) in a growth medium comprising EGF to obtain mature keratinocytes.

3. The method of claim 1, wherein the hEpSCs in step (e) are cultured in a chamber with fibroblasts to obtain hair follicles.

* * * * *

UNITED STATES PATENT AND TRADEMARK OFFICE
CERTIFICATE OF CORRECTION

PATENT NO. : 10,080,771 B2
APPLICATION NO. : 15/009157
DATED : September 25, 2018
INVENTOR(S) : Xiaowei Xu et al.

Page 1 of 1

It is certified that error appears in the above-identified patent and that said Letters Patent is hereby corrected as shown below:

In the Specification

Column 1, after Line 11 and before the heading "FIELD OF THE INVENTION", insert the following heading and paragraph:
-- GOVERNMENT SUPPORT CLAUSE
This invention was made with government support under grant number AR054593 awarded by the National Institutes of Health. The government has certain rights in the invention. --

Signed and Sealed this
Nineteenth Day of February, 2019

Andrei Iancu
*Director of the United States Patent and Trademark Office*